(12) United States Patent
Bernards et al.

(10) Patent No.: US 6,303,335 B1
(45) Date of Patent: Oct. 16, 2001

(54) TRANSCRIPTION FACTOR E2F-4

(75) Inventors: Réné Bernards; Roderick L. Beijersbergen, both of Amsterdam (NL)

(73) Assignee: Prolifix Limited, Oxon (GB)

( * ) Notice: Subject to any disclaimer, the term of this patent is extended or adjusted under 35 U.S.C. 154(b) by 0 days.

(21) Appl. No.: 09/265,566

(22) Filed: Mar. 10, 1999

Related U.S. Application Data

(63) Continuation of application No. 08/836,582, filed as application No. PCT/GB95/00868 on Apr. 18, 1995, now Pat. No. 6,045,999.

(51) Int. Cl.⁷ .............................. C12P 21/02; C12N 5/10; C12N 15/12; C12N 15/63
(52) U.S. Cl. .................... 435/69.1; 435/320.1; 435/325; 435/366; 536/23.5
(58) Field of Search ................................ 435/320.1, 325, 435/366, 69.1; 536/23.1, 23.5

(56) References Cited

U.S. PATENT DOCUMENTS 6,045,999 * 4/2000 Bernards et al. .

FOREIGN PATENT DOCUMENTS

WO 93/15227 8/1993 (WO) .
WO 94/10307 5/1994 (WO) .

OTHER PUBLICATIONS

M. Ivey–Hoyle et al., "Cloning and Characterization of E2F–2, a Novel Protein with the Biochemical Properties of Transcription Factor E2F", Molecular and Cellular Biology, vol. 13, pp. 7802–7812 Dec. 1993.

N. Dyson et al., "Analysis of; 107–Associated Proteins: p107 Associates With a Form of E2F That Differs From pRB–Associated E2F–1", Journal of Virology, vol. 67, No. 12, pp. 7641–7647 Dec. 1993.

Ayer et al., "Mad: A Heterodimeric Partner for Max That Antagonizes Myc Transcriptional Activity", Cell, vol. 72, pp. 211–222, Jan. 29, 1993.

Ginsberg et al., "E2F–4, A New Member of the E2F Gene Family, Has Oncogenic Activity and Associates with p107 in vivo", Genes & Development, vol. 8, No. 22, pp. 2665–2692, Nov. 15, 1994.

Bernards et al., "Identification and Cloning of Proteins that Associate with p107, a Relative of the Retinoblastoma Protein", (Abstract), EMBL Conference, Heidelberg, Germany Apr. 18–21, 1994.

Beijeersbergen et al., "E2F–4, a New Member of the E2F Gene Family, has Oncogenic Activity and Associates with p107 in vivo", Genes & Development, vol. 8, No. 22, pp. 2665–2792, Nov. 15, 1994.

* cited by examiner

Primary Examiner—Robert A. Schwartzman
(74) Attorney, Agent, or Firm—Nixon & Vanderhye P.C.

(57) ABSTRACT

A novel transcription factor, belong to the E2f gene family, is disclosed. This is called E2F-4. It interacts with DP-1 and can be regulated by p107.

11 Claims, 9 Drawing Sheets

Fig.1A-1

```
        10                  30                  50                  70                  90
CAGTCGACCCCGGGGGGGGGGCCGATGGGCGGAGGCCGGGGAGGCCGCGGCCACAGGCCGCCGGGACTCCAAGCCGGCACGAAAAGAGCCTGGGACTGCT
                         M  A  E  A  G  P  Q  A  P  P  P  P  G  T  P  S  R  H  E  K  S  L  G  L  L
        110                 130                 150                 170                 190
CACCACCAAGTTCGTGTCCCTTCTGCAGGAGGCCAAGGACGGCGTGCTTGACCTCAAGCTGCTTGCAGCTGACACCCTAGCTGTACGCCAGAAGCGGCGGATT
 T  T  K  F  V  S  L  L  Q  E  A  K  D  G  V  L  D  L  K  L  L  A  A  D  T  L  A  V  R  Q  K  R  R  I
        210                 230                 250                 270                 290
TACGACATTACCAATGTTTTGGAAGGTATCGGGCTAATCGAGAAAAAGTCCAAGAACAGCATCCAGTGGAAGGGTGTGGGGCCTGGCTGCAATACCCGGG
 Y  D  I  T  N  V  L  E  G  I  G  L  I  E  K  K  S  K  N  S  I  Q  W  K  G  V  G  P  G  C  N  T  R  E
        310                 330                 350                 370                 390
AGATTGCTGACAAACTGATTGAGCTCAAGGCAGAGATCGAGGAGCTGCAGCAGCGGGAGCAAGAACTAGACCAGCACAAGGTGTGGGTGCAGCAGAGCAT
 I  A  D  K  L  I  E  L  K  A  E  I  E  E  L  Q  Q  R  E  Q  E  L  D  Q  H  K  V  W  V  Q  Q  S  I
        410                 430                 450                 470                 490
CCGGAACGTCACAGAGGACGTGCAGAACAGCTGTGTTGGCCTACGTGCTTTGCTGAGATACTGAGGACATCTGCAGATGCTTTGCTGAGATACCCTCTTGGCCATCCGG
 R  N  V  T  E  D  V  Q  N  S  C  L  A  Y  V  T  H  E  D  I  C  R  C  F  A  G  D  T  L  L  A  I  R
        510                 530                 550                 570                 590
GCCCCATCAGGACGCCTGGAGGTCCCAGCTGCCCATCCCCAGAGGGTCTCAATGGGCAGAAGAAGTACCAGATTCACCTGAAGAGTGTGAGTGGTCCCATTGAGG
 A  P  S  G  T  S  L  E  V  P  I  P  E  G  L  N  G  Q  K  K  Y  Q  I  H  L  K  S  V  S  G  P  I  E  V
        610                 630                 650                 670                 690
TTCTGCTGGTGAACAAGGAGGCCATGAGCTCACCCCCTGCCGTGGCTGTGCCACCTCCACCTCCTGAAGATTTGCTGCTCACCTGAAGATTTGCTGCTCACCTGAGATTTGCTGTTTCTACACC
 L  L  V  N  K  E  A  W  S  S  P  P  V  A  V  P  P  P  P  E  D  L  L  Q  S  P  S  A  V  S  T  P
        710                 730                 750                 770                 790
TCCACCTGCCCTGCCCAAGCCTGCCCTAGCCACGTCCAGTCCCAGGAAGCCTCACGTCCAAATAGTCCTCAGCTCCCAGCTGTCCCTGCTGTCCCTGCTGTCCCTGCTGTCCCTGCAGTCGCAGAAGTC
 P  P  L  P  K  P  A  L  A  Q  S  Q  E  A  S  R  P  N  S  P  Q  L  T  P  T  A  V  P  G  S  A  E  V
```

Fig. 1A-2

```
               810                830                850                870                890
CAGGGAATGGCTGGCCCAGCAGCTGAGATCAACAGTGAGTGGGGGCCCTGGGACTGATAGCAAGGACAGTGGTGAGCTCAGTTCACTCCCACTGGGCCCAA
 Q  G  M  A  G  P  A  A  E  I  T  V  S  G  G  P  G  T  D  S  K  D  S  G  E  L  S  S  L  P  L  G  P  T 910                930                950                970                990
CAACACTGGACACCCGGCCACTGCAGTCTTCTGCCCTGCTGGACAGCAGCAGCAGCAGCAGCAGCAGCAACAGTAACAGCAGCAG
 T  L  D  T  R  P  L  Q  S  S  A  L  L  D  S  S  S  S  S  S  S  S  S  S  N  S  N  S  S  S 1010               1030               1050               1070               1090
TTCGTCCGGACCCAACCCTTCTACTCCTTTGAGCCCATCAAGGCAGACCCCACAGGTGTTTTGAACTCCCCAAAGAGCTGTCAGAAATCTTTGATCCC
 S  S  G  P  N  P  S  T  S  F  E  P  I  K  A  D  P  T  G  V  L  E  L  P  K  E  L  S  E  I  F  D  P 1110               1130               1150               1170               1190
ACACGAGAGTGCATGAGCTCGGAGCTGCTGGAGGAGTTGATGTCCTCAGAAGTGTTTGCCCCTCTGCTTCGTCTTTCTCACCCCGGGAGACCACGATT
 T  R  E  C  M  S  S  E  L  L  E  E  L  M  S  S  E  V  F  A  P  L  L  R  L  S  P  P  P  G  D  H  D  Y 1210               1230               1250               1270               1290
ATATCTACAACCTGGACGAGAGTGAAGGTGTCTGTGACCTCTTTGATGTCCTGTTCTCAACCTGACTGACAGGGACATGCCCTGTGTGGCTGTGGGACC
 I  Y  N  L  D  E  S  E  G  V  C  D  L  F  D  V  P  V  L  N  L  *

1310               1330               1350               1370               1390
ATATCTACAACCTGGACGAGAGTGAAGGTGTCTGTGACCTCTTTGATGTCCTGTTCTCAACCTGACTGACAGGGACATGCCCTGTGTGGCTGTGGGACC
CAGACTGTCTGACCTGGGGTTGCCTGGGGCTGCCCACCCGACCCCTACAGAGCTTGAGAGCCACAGACGAATGGCTTCTCCGGNATTNCCTTACCG 1410               1430               1450               1470
CACAGTTCTGGCCACACGTCCCGCTCCTCCTGTGCTGCTCGCAGAGCAGGGAACAGGACTCAGCCCCCCATCACCGTGGAG
```

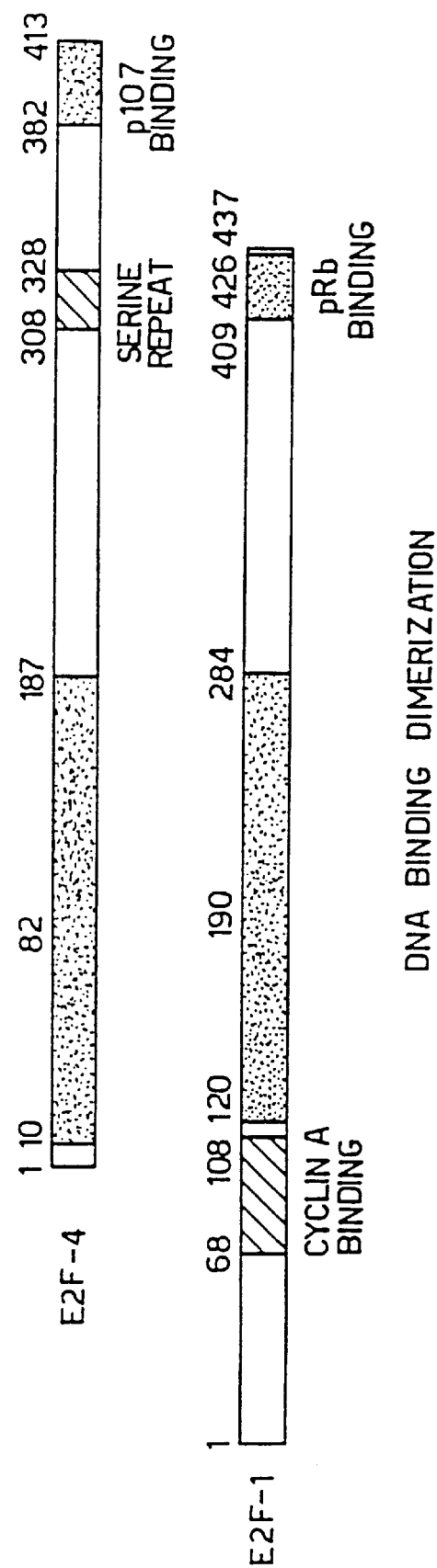

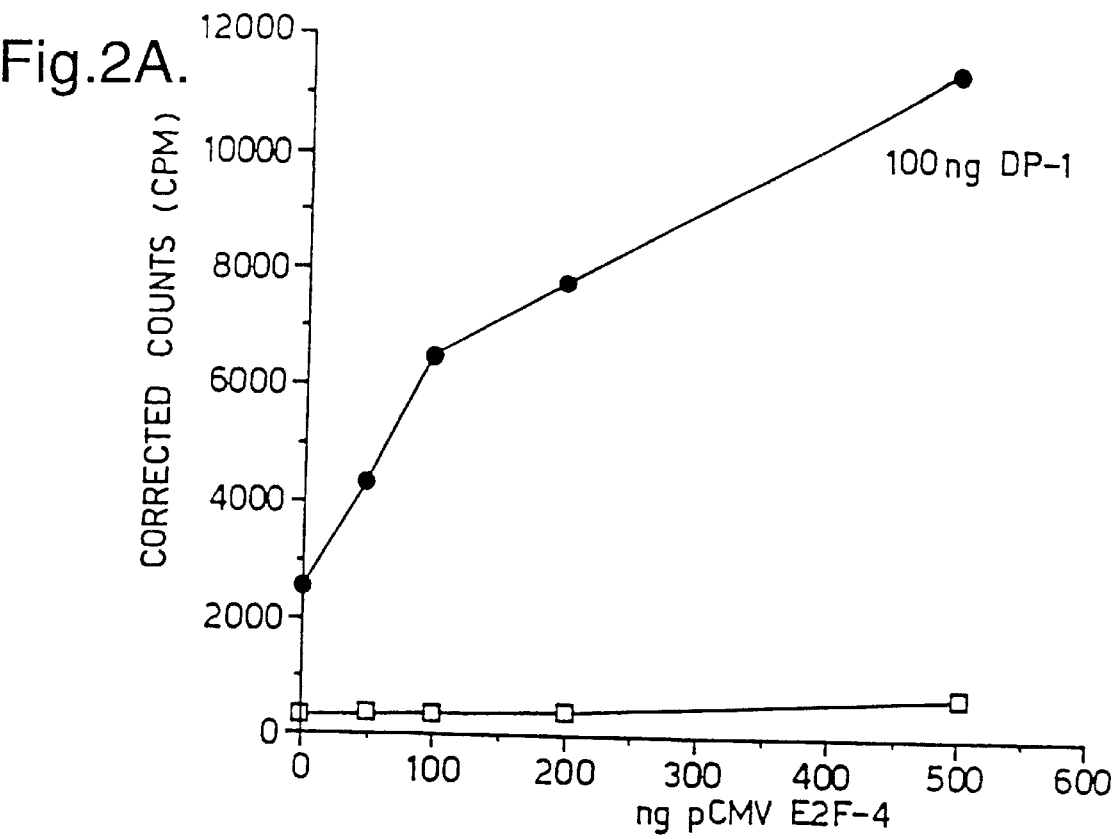
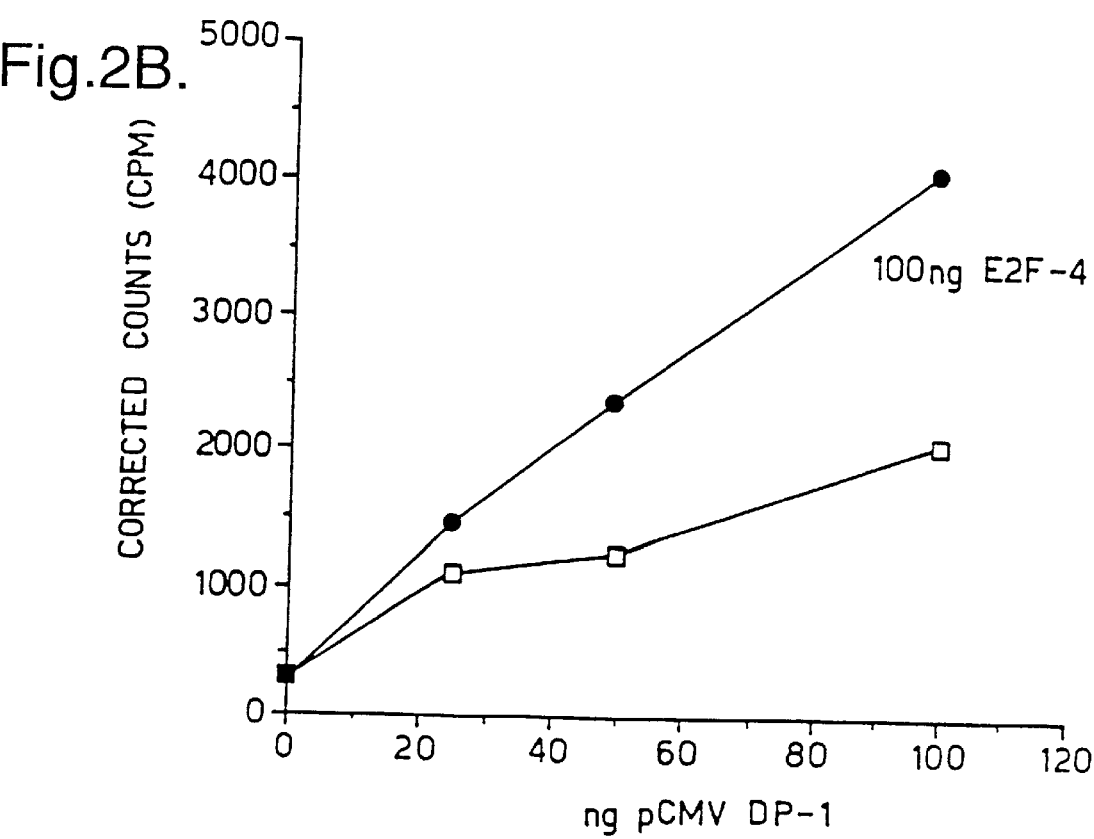

TRANSCRIPTION FACTOR E2F-4

This is a continuation of application Ser. No. 08/836,582, filed May 14, 1997, U.S. Pat. No. 6,040,999 which is a 371 of PCT/GB95/00868 filed Apr. 18, 1995 allowed Nov. 1, 1998.

This invention relates to a novel transcription factor and to its production and uses.

The molecular events that occur during the cell cycle need to be impregnated with the transcription apparatus so that gene expression can be synchronised with cell cycle progression.

Recently, a transcription factor called E2F (or DRTF1) has been identified and shown to bind to pRb, the protein product of the retinoblastoma susceptibility gene, an anti-oncogene or tumour suppressor gene (see for example Wagner and Green, Nature 352, 189–190, 1991). It is widely believed that the cellular transcription factor E2F functions as a key component in cell cycle control because it associates with important cell cycle regulating proteins, such as the retinoblastoma gene product (pRb), p107, cyclins and cyclin-dependent kinases, and furthermore its transcriptional activity is modulated by certain viral oncoproteins, such as adenovirus Ela, SV40 large T antigen, and the human papilloma virus E7 protein.

It is believed that the transcription factor E2F (or DRTF1) plays an important role in integrating cell cycle events with the transcription apparatus because, during cell cycle progression in mammalian cells, it undergoes a series of periodic interactions with molecules that are known to be important regulators of cellular proliferation. For example, the retinoblastoma tumor suppressor gene product (pRb), which negatively regulates progression from G1 into S phase, and is frequently modified in tumour cells, binds to E2F. Similarly, the pRb-related protein p107 occurs predominantly in an S phase complex with E2F. Both pRb and p107 repress the transcriptional activity of E2F, which is likely to be fundamentally important for regulating cellular proliferation because E2F binding sites (the E2F site) occur in the control regions of a variety of genes that are involved with proliferation, such as c-myc and $p34^{cdc2}$. Furthermore, mutant Rb proteins, encoded by alleles isolated from tumour cells, fail to bind to E2F, and hence are unable to interfere with E2F site-dependent transcriptional activation. Another important feature of E2F is that certain viral oncoproteins, such as adenovirus Ela, SV40 large T antigen and human papilloma virus E7, modulate its activity by sequestering pRb and p107 from the inactive transcription factor. This effect requires regions in these viral proteins that are necessary for transformation of tissue culture cells and hence to overcome growth control. Thus, the ability of these oncoproteins to regulate E2F may be the means by which they over-ride the normal mechanisms of cellular growth control and, conversely, transcriptional repression by pRb may be the basis of pRb-mediated negative growth control.

A potential mechanism for integrating the transcription-regulating properties of pRb and p107 with other cell cycle events was suggested by the identification of cyclin A and the cdc2-related cyclin-dependent kinase $p33^{cdk2}$ in the E2F complex. Cyclin A is necessary for progression through S phase, a function that could perhaps be mediated through its ability to recruit the cyclin-dependent kinase $p33^{cdk2}$ to E2F. Taken together these data suggest that E2F is a transcription factor whose primary role may be to relay cell cycle events to the transcription apparatus via molecules such as pRb, p107, cyclins and cdks, thus ensuring that gene expression is synchronised and integrated with cell cycle progression.

More recently, a transcription factor with the properties of E2F has been cloned and sequenced (Helin et al, Cell 70 (1992), 337–350 and Kaelin et al, Cell 70 (1992), 351–364).

DISCLOSURE OF THE INVENTION

We have now surprisingly found a further new protein which appears to be a new member of the E2F gene family, which we have called E2F-4. The cDNA sequence of E2F-4 is presented in FIG. 1A, as is the amino acid sequence of this protein. This new protein is referred to as E2F-4 and this nomenclature will be used in this specification.

It has been found that E2F-4 is one of a family of related transcription factor components. Members of this family are believed to interact with DP proteins to form a series of transcription factors. DP protein (or polypeptides) include DP-1, DP-2 and DP-3 although the first of these will usually be contemplated in preference to the other two.

FIGS. 1A-1 and 1A-2 show the nucleotide sequence of the E2F-4 cDNA (SEQ ID NO:1). The first 74 bp was derived from mouse E2F-4, and the remainder from human E2F-4.

FIG. 1B shows a schematic representation of E2F-4 in comparison with E2F-1. Black and shaded boxes are regions of high homology; hatched regions are specific for E2F-4 or E2F-1.

FIG. 2A shows E2F-4 with DP-1 cooperate in trans-activation. C33A cells were transfected with increasing amounts of pCMV-E2F-4 (lower curve) or with increasing amounts pCMV-E2F-4 together with 100 ng of pCMVDP-1 (upper curve) together with 2 μg of reporter construct (E2F$_4$ CAT) and 0.2 μg of RSV luciferase as an internal control. CAT activity was normalised to the luciferase activity for each sample (corrected counts). CAT activities are the average of duplicate samples.

FIG. 2B shows the results of C33A cells transfected as described in FIG. 2A, except that pCMV-DP-1 was transfected in increasing amounts (lower curve) or increasing amounts of pCMV-DP-1 in combination with 100 ng of pCMV-E2F-4 (upper curve). CAT activity was calculated as in A.

Figure 3:
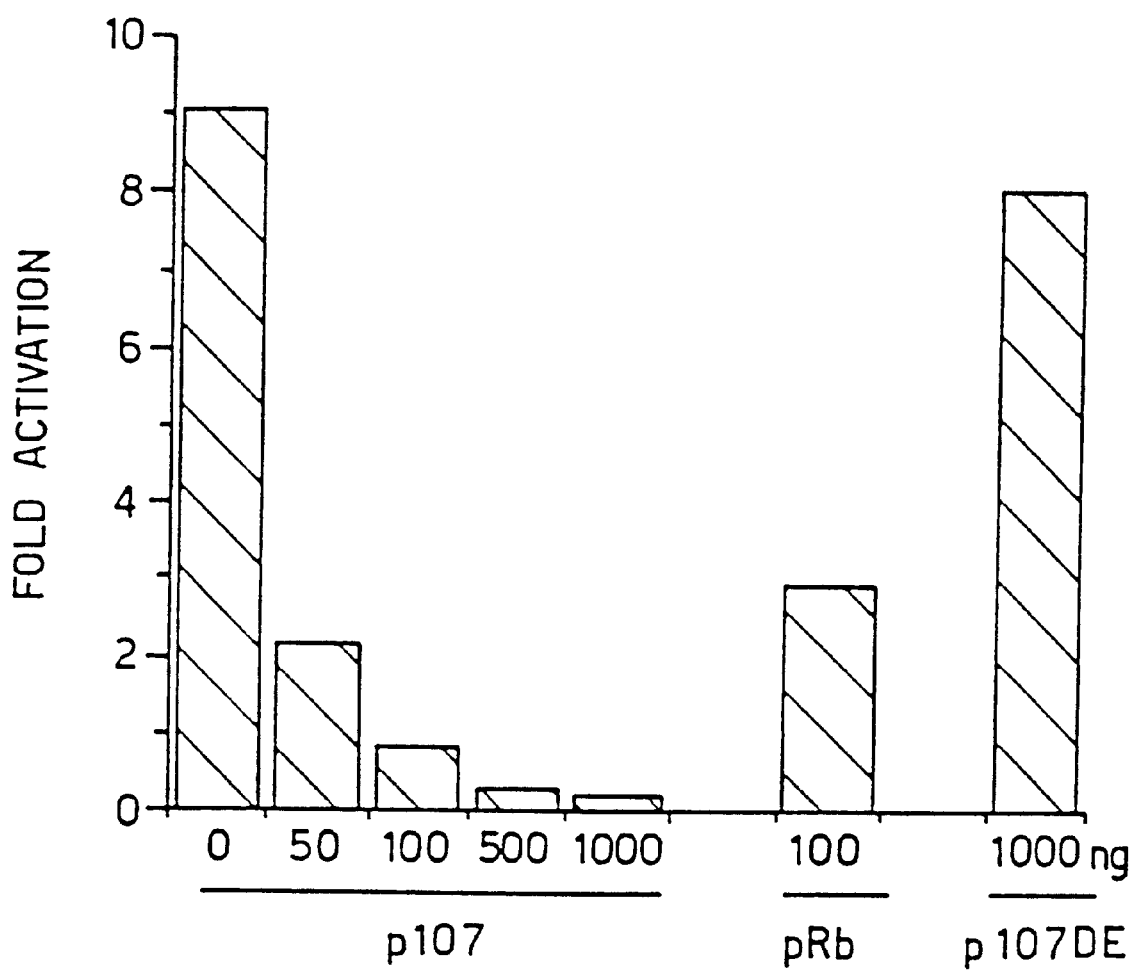

FIG. 3 shows p107 inhibits E2F-4 mediated trans-activation. C33A cells were transfected with 100 ng of pCMV-E2F-4 and 100 ng of pCMV-DP-1 in combination with increasing amounts of pCMV-p107, 100 ng of pRb, or 1000 ng of pCMV-p107-DE. Together with the expression plasmids, the cells were transfected with 2 μg of E2F$_4$CAT and 0.2 μg of pRSV luciferase. CAT activity was normalized to the luciferase internal control. Fold activation was calculated relative to the basal level of E2F$_4$CAT, which was set to unity (1.0). Data was representative of at least three independent experiments performed in duplicate.

Figure 4A:
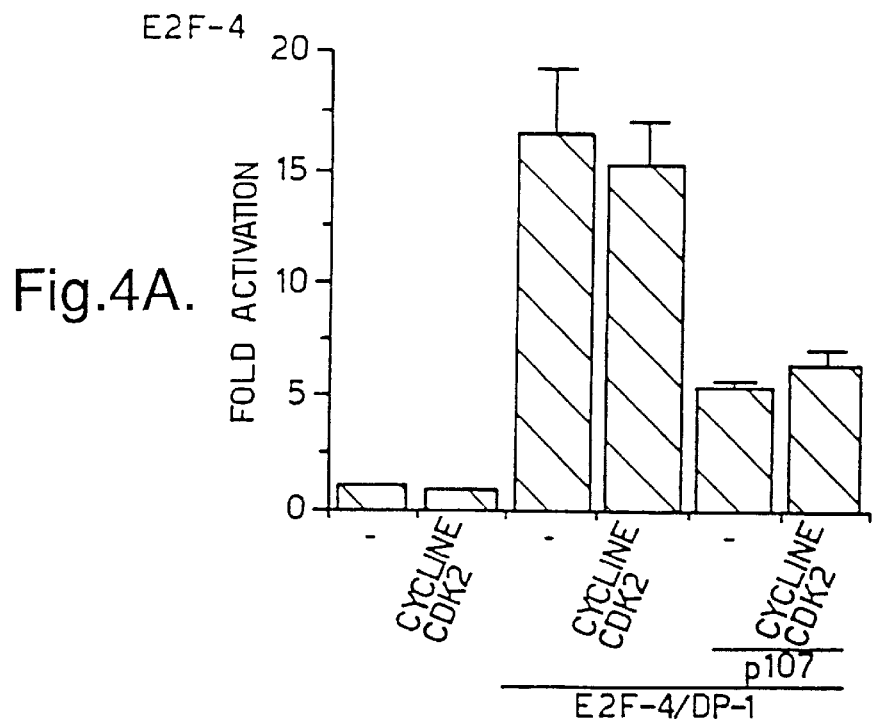

FIG. 4A shows the effect of cyclin E/cdk2 on p107-E2F and pRb-E2F interactions. C33A cells were transfected with 100 ng pCMVE2F-4 and 100 ng pCMVDP-1 in combination with 200 ng of pCMVp107 and with 2.0 μg pCMVcyclin E and 20 μg pCMVcdk2 as indicated. Together with the expression plasmids, the cells were transfected with 2 μg E2F$_4$-CAT and 0.2 μg pRSV luciferase. CAT activity was normalized to the luciferase internal control. Fold activation was calculated relative to basal level of E2F$_4$-CAT which was set to unity (1.0). The experiments were performed in duplicate and activity was also assayed in duplicate. Data are representative for at least three independent experiments.

Figure 4B:
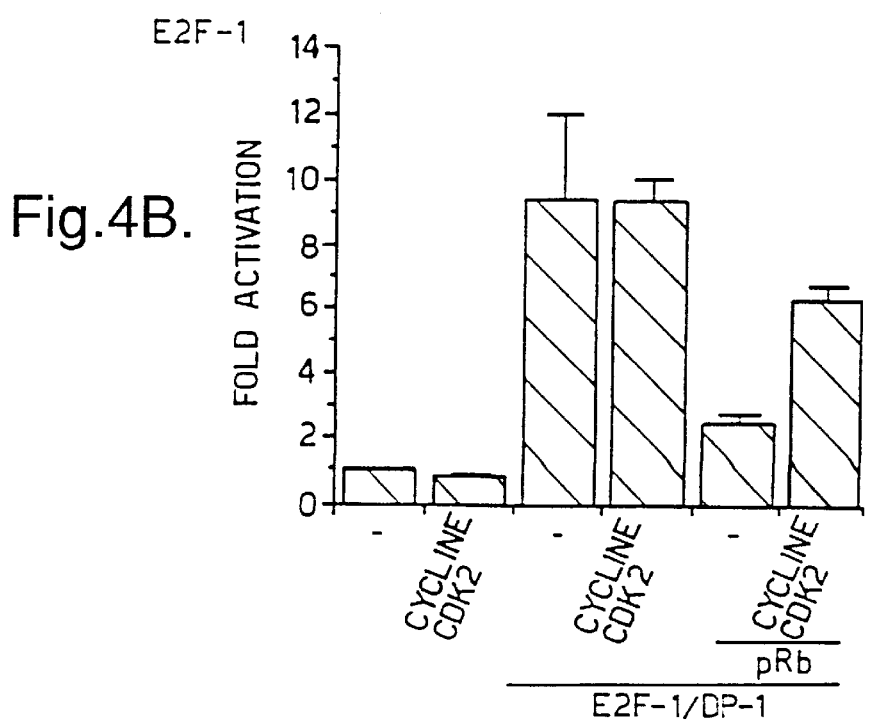

FIG. 4B shows C33A cells transfected with 100 ng pCMVE2F-1 and 100 ng pCMVDP-1 in combination with 200 ng pCMVpRB and with 2.0 μg pCMVcyclin E and 2.0

μg pCMVcdk2 as indicated. Fold activation was determined as described in FIG. 4A.

Figure 5A:
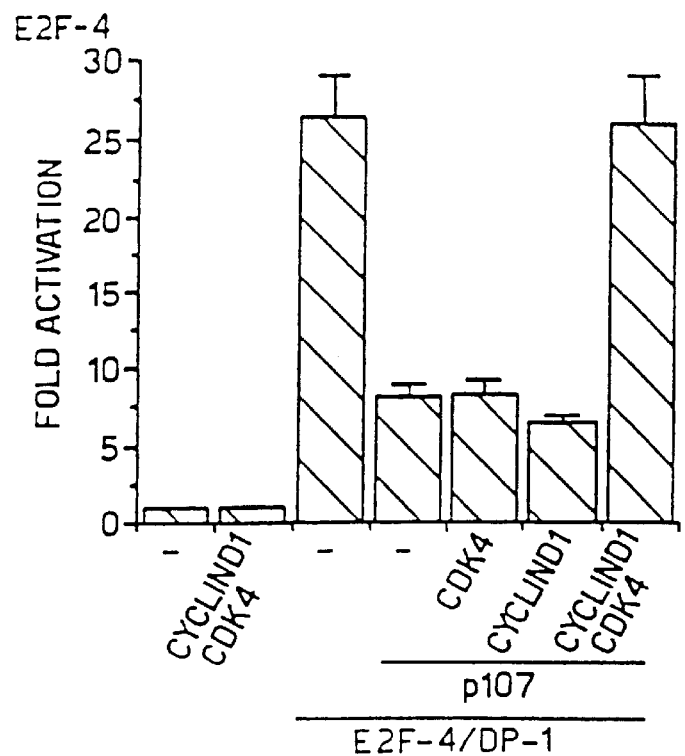

FIG. 5A shows the effect of cyclin D1 and cdk4 on p107 and pRb. C33A cells were transfected with 100 ng pCMVE2F-4 and 100 ng pCMVDP-1 in combination with 200 ng pCMVp107 and with 2.0 μg pCMVcyclin D1 and 2.0 μg pCMVcdk4 as indicated. Together with the expression plasmids, the cells were transfected with 2 μg E2F$_4$-CAT and 0.2 μg pRSV luciferase.

Figure 5B:
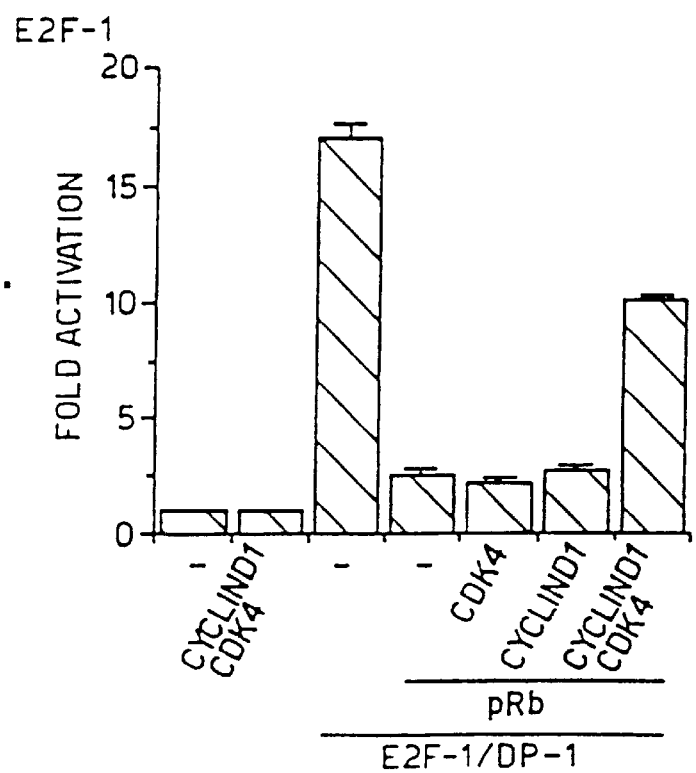

FIG. 5B shows C33A cells transfected with 100 ng pCMVE2F-1 and 100 ng pCMVDP-1 in combination with 200 ng pCMVpRB and with 2.0 μg pCMVcyclin D1 and 2.0 μg pCMVcdk4 as indicated. Experiments were performed as described in FIG. 1A. Fold activation was calculated as described in FIG. 1A.

Figure 6:
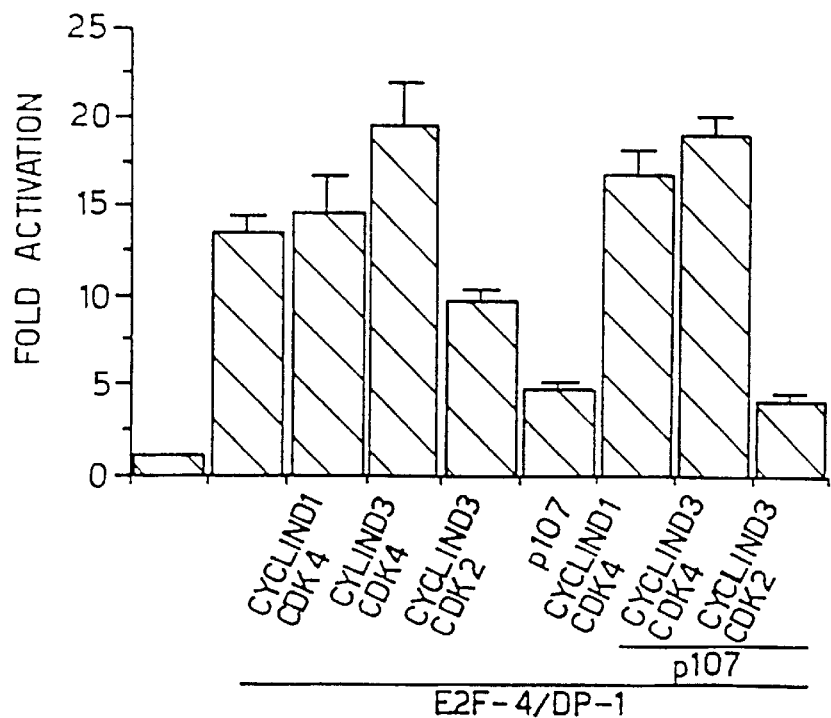

FIG. 6 shows a cyclin D1 and D3 in combination with cdk4 can release p107 inhibition. Cells were transfected as described in FIG. 2. 2.0 μg cyclin D1, cyclin D3, cdk2 mutants or cdk4 were co-transfected as indicated.

Figure 7:
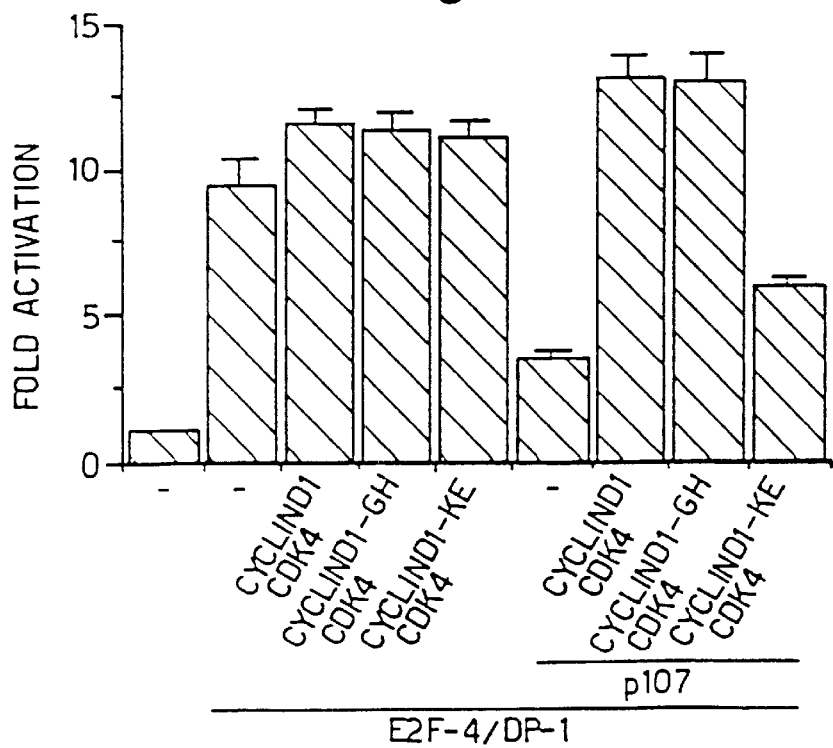

FIG. 7 shows the effect of cyclin D1 on p107/E2F-4. C33A cells were transfected as described in FIG. 3. 2.0 μg pCMVcyclin D1 KH, mutant cyclin D1 that carries a mutation in the LXCXE domain, or 2.0 μg pCMVcyclin D1 KE, mutant cyclin D1 that lacks the cdk4 interaction site, were transfected as indicated.

Figure 8A:
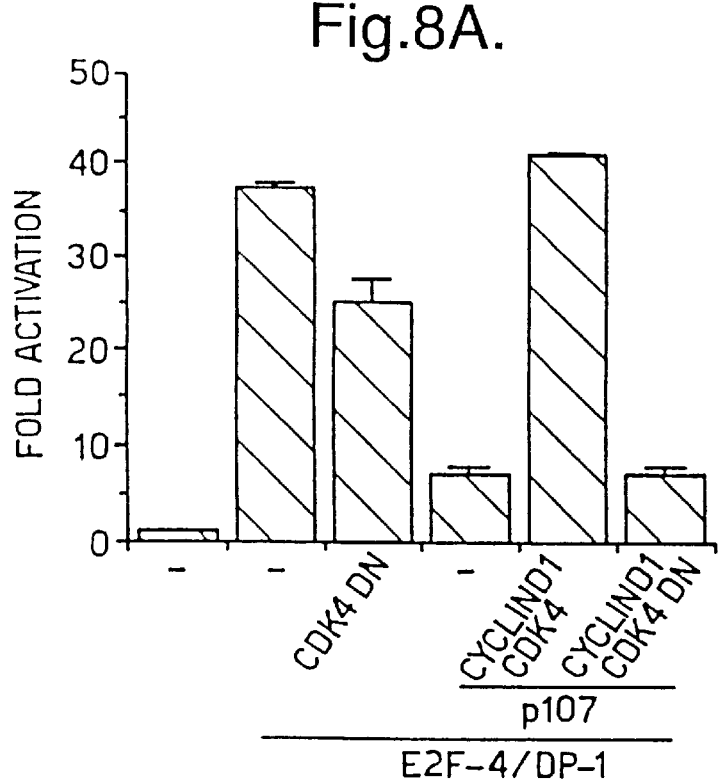

FIG. 8A shows that cyclin D1 in combination with a dominant negative cdk4 cannot release p107 inhibition. C33A cells were transfected as described in FIG. 2, 2.0 μg cdk4 dominant negative (cdk4DN) was transfected as indicated.

Figure 8B:
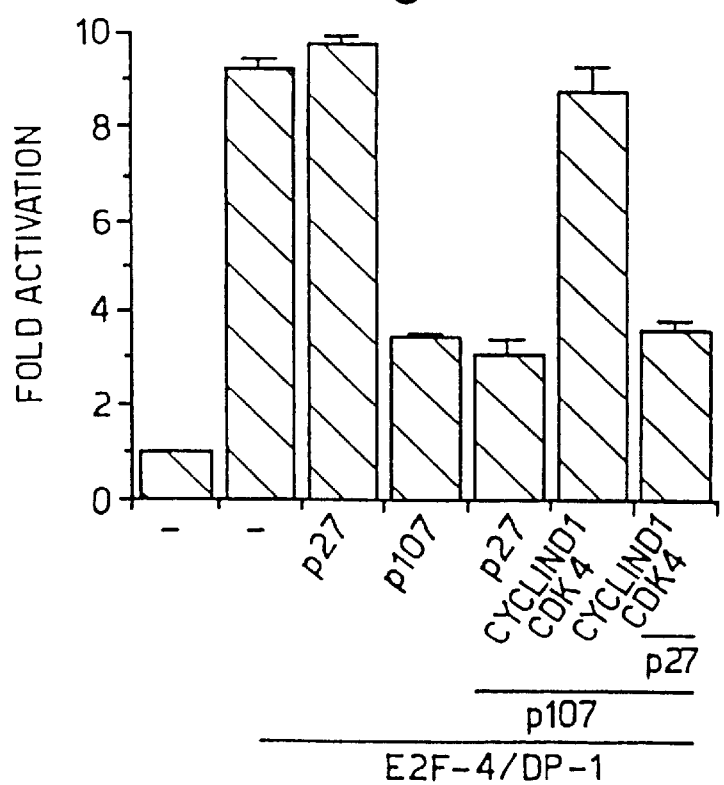

FIG. 8B shows the release of p107 inhibition by cyclin D1/cdk4 is blocked by p27$^{kip1}$. C33A cells were transfected as described in FIG. 2. 2.0 μg p27$^{kip1}$ was transfected as indicated.

DETAILED DESCRIPTION OF THE INVENTION

The invention in a first aspect provides a protein as shown in FIG. 1A, homologues thereof, and fragments of the sequence and its homologues, which is capable of functioning as a mammalian transcription factor. In particular, the invention provides a polypeptide (preferably in substantially isolated form) comprising:

(a) E2F-4;

(b) the protein of FIG. 1A;

(c) a mutant, allelic variant or species homologue of (a) or (b);

(d) a protein at least 70% homologous to (a) or (b);

(e) a fragment of any one of (a) to (d) capable of forming a complex with a DP protein, pRb, p107 and/or p130; or (f) a fragment of any of (a) to (e) of at least 15 amino acids long.

All polypeptides within this definition are referred to below as polypeptide(s) according to the invention.

The proteins pRb, p107, DP proteins and p130 are referred to herein as complexing proteins or "complexes" as they may form a complex with the proteins of the invention. Under certain conditions E2F-4 may not bind, or may only bind weakly, to pRb.

A polypeptide of the invention will be in substantially isolated form if it is in a form in which it is free of other polypeptides with which it may be associated in its natural environment (eg the body). It will be understood that the polypeptide may be mixed with carriers or diluents which will not interfere with the intended purpose of the polypeptide and yet still be regarded as substantially isolated.

The polypeptide of the invention may also be in a substantially purified form, in which case it will generally comprise the polypeptide in a preparation in which more than 90%, eg. 95%, 98% or 99% of the polypeptide in the preparation is a polypeptide of the invention.

Mutant polypeptides will possess one or more mutations which are additions, deletions, or substitutions of amino acid residues. Preferably the mutations will not affect, or substantially affect, the structure and/or function and/or properties of the polypeptide. Thus, mutants will suitably possess the ability to be able to complex with DP proteins, pRb, p107 and/or p130. Mutants can either be naturally occurring (that is to say, purified or isolated from a natural source) or synthetic (for example, by performing site-directed mutagenesis on the encoding DNA. It will thus be apparent that polypeptides of the invention can be either naturally occurring or recombinant (that is to say prepared using genetic engineering techniques). An allelic variant will be a variant which will occur naturally in an, eg. murine, animal and which will function to regulate gene expression in a substantially similar manner to the protein in FIG. 1A.

Similarly, a species homologue of the protein will be the equivalent protein which occurs naturally in another species, and which performs the equivalent function in that species to the protein of FIG. 1A in another (eg. mammalian) animals. Within any one species, a homologue may exist as several allelic variants, and these will all be considered homologues of the protein. Allelic variants and species homologues can be obtained by following the procedures described herein for the production of the protein of FIG. 1A and performing such procedures on a suitable cell source, eg from a rodent, carrying an allelic variant or another species. Since the protein may be evolutionarily conserved it will also be possible to use a polynucleotide of the invention to probe libraries made from rodent or other cells in order to obtain clones encoding the allelic or species variants. The clones can be manipulated by conventional techniques to identify a polypeptide of the invention which can then be produced by recombinant or synthetic techniques known per so. Preferred species homologues include mammalian or amphibian species homologues.

A protein at least 70% homologous to that in FIG. 1A is included in the invention, as are proteins at least 80 or 90% and more preferably at least 95% homologous to the protein of FIG. 1A. This will generally be over a region of at least 20, preferably at least 30, for instance at least 40, 60 or 100 or more contiguous amino acids. Methods of measuring protein homology are well known in the art and it will be understood by those of skill in the art that in the present context. Homology is usually calculated on the basis of amino acid identity (sometimes referred to as "hard homology").

Generally, fragments of FIG. 1A or its allelic variants or species homologues thereof capable of forming a complex with the complexors will be at least 10, preferably at least 15, for example at least 20, 25, 30, 40, 50 or 60 amino acids in length.

It will be possible to determine whether fragments form a complex with the complex of proteins by providing the complexor protein and the fragment under conditions in which they normally form a complex, such as a transactivating transcription factor, and determining whether or not a complex has formed. The determination may be made by, for example, measuring the ability of the complex to bind an EF2 binding site in vitro, or alternatively, determining the molecular weight of the putative complex by methods such as SDS-PAGE.

Preferred fragments include those which are capable of forming a trans-activation complex with DP-1 or other complexors. The examples herein describe a number of methods to analyse the function of the protein and these may be adapted to asses whether or not a polypeptide is capable of forming a trans-activation complex with the DP-1 protein. For example, the polypeptide can be added to the complexor in the presence of a reporter gene construct adapted to be activated by the DP-1/E2F-4 complex (for example, see FIG. 10 of WO-A-94/10307 in the name of the Medical Research Council). Such an experiment can determine whether the polypeptide fragment has the necessary activity.

A polypeptide of the invention may be labelled with a revealing or detectable label. The (revealing) label may be any suitable label which allows the polypeptide to be detected. Suitable labels include radioisotopes, e.g. $^{125}$I, enzymes, antibodies and linkers such as biotin. Labelled polypeptides of the invention may be used in diagnostic procedures such as immunoassays in order to determine the amount of E2F-4 protein in a sample.

A polypeptide or labelled polypeptide according to the invention may also be attached or fixed to a solid phase or support, for example the wall of an immunoassay dish.

A second aspect of the invention relates to a polynucleotide which comprises:

(a) a sequence of nucleotides shown in FIG. 1A;

(b) a sequence complementary to (a);

(c) a sequence capable of selectively hybridising to a sequence in either (a) or (b);

(d) a sequence encoding a polypeptide as defined in the first aspect; or (e) a fragment of any of the sequences in (a) to (d).

The present invention thus provides a polynucleotide, suitably in substantially isolated or purified form, which comprises a contiguous sequence of nucleotides which is capable of selectively hybridizing to FIG. 1A or to its complement. Polynucleotides of the invention include a DNA of FIG. 1A and fragments thereof capable of selectively hybridizing to the sequence of FIG. 1A. A further embodiment of the invention provides a DNA coding for the protein in FIG. 1A or a fragment thereof.

The polynucleotide may also comprise RNA. It may also be a polynucleotide which includes within it synthetic or modified nucleotides. A number of different types of modification to oligonucleotides are known in the art. These include methylphosphonate and phosphorothionate backbones, addition of acridine or polylysine chains at the 3' and/or 5' ends of the molecule. For the purposes of the present invention, it is to be understood that the oligonucleotides described herein may be modified by any method available in the art. Such modifications may be carried out in order to enhance the in vivo activity or lifespan of oligonucleotides of the invention used in methods of therapy.

A polynucleotide capable of selectively hybridizing to the DNA of FIG. 1A will be generally at least 70%, preferably at least 80 or 90% and optimally at least 95% homologous to the DNA of FIG. 1A over a region of at least 20, preferably at least 30, for instance at least 40, 60 or 100 or more contiguous nucleotides. These polynucleotides are within the invention.

A polynucleotide of the invention will be in substantially isolated form if it is in a form in which it is free of other polynucleotides with which it may be associated in its natural environment (usually the body). It will be understood that the polynucleotide may be mixed with carriers or diluents which will not interfere with the intended purpose of the polynucleotide and it may still be regarded as substantially isolated.

A polynucleotide according to the invention may be used to produce a primer, e.g. a PCR primer, a probe, e.g. labelled with a revealing or detectable label by conventional means using radioactive or non-radioactive labels, or the polynucleotide may be cloned into a vector. Such primers, probes and other fragments of the DNA of FIG. 1A will be at least 15, preferably at least 20, for example at least 25, 30 or 40 nucleotides in length, and are also encompassed within the invention.

Polynucleotides, such as a DNA polynucleotides according to the invention may be produced recombinantly, synthetically, or by any means available to those of skill in the art. It may be also cloned by reference to the techniques disclosed herein.

The invention includes a double stranded polynucleotide comprising a polynucleotide according to the invention and its complement.

A third aspect of the invention relates to an (eg. expression) vector suitable for the replication and expression of a polynucleotide, in particular a DNA or RNA polynucleotide, according to the invention. The vectors may be, for example, plasmid, virus or phage vectors provided with an origin of replication, optionally a promoter for the expression of the polynucleotide and optionally a regulator of the promoter. The vector may contain one or more selectable marker genes, for example an ampicillin resistance gene in the case of a bacterial plasmid or a neomycin resistance gene for a mammalian vector. The vector may be used in vitro, for example for the production of RNA or used to transfect or transform a host cell. The vector may also be adapted to be used in vivo, for example in a method of gene therapy.

Vectors of the third aspect are preferably recombinant replicable vectors. The vector may thus be used to replicate the DNA. Preferably, the DNA in the vector is operably linked to a control sequence which is capable of providing for the expression of the coding sequence by a host cell. The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences. Such vectors may be transformed or transfected into a suitable host cell to provide for expression of a polypeptide of the invention.

A fourth aspect of the invention thus relates to host cells transformed or transfected with the vectors of the third aspect. This may be for the replication and expression of a polynucleotide according to the invention, including the sequence of FIG. 1A or the open reading frame thereof. The cells will be chosen to be compatible with the vector and may for example be bacterial, yeast, insect or mammalian.

A polynucleotide according to the invention may also be inserted into the vectors described above in an antisense orientation in order to provide for the producing of antisense RNA. Antisense RNA or other antisense polynucleotides may also be produced by synthetic means. Such antisense polynucleotides may be used in a method of controlling the levels of the E2F-4 protein in a cell. Such a method may include introducing into the cell the antisense polynucleotide in an amount effective to inhibit or reduce the level of translation of the E2F-4 mRNA into protein. The cell may be a cell which is proliferating in an uncontrolled manner such as a tumour cell.

Thus, in a fifth aspect the invention provides a process for preparing a polypeptide according to the invention which comprises cultivating a host cell transformed or transfected with an (expression) vector of the third aspect under conditions providing for expression (by the vector) of a coding sequence encoding the polypeptide, and recovering the expressed polypeptide.

The invention in a sixth aspect also provides (monoclonal or polyclonal) antibodies to a polypeptide according to the invention. Antibodies of the invention include fragments, thereof as well as mutants that retain the antibody's binding activity. The invention further provides a process for the production of monoclonal or polyclonal antibodies to a polypeptide of the invention. Monoclonal antibodies may be prepared by conventional hybridoma technology using the proteins or peptide fragments thereof as an immunogen. Polyclonal antibodies may also be prepared by conventional means which comprise inoculating a host animal, for example a rat or a rabbit, with a polypeptide of the invention and recovering immune serum.

Fragments of monoclonal antibodies which can retain their antigen binding activity, such Fv, F(ab') and F(ab$_2$)' fragments are included in this aspect of the invention. In addition, monoclonal antibodies according to the invention may be analyzed (eg. by DNA sequence analysis of the genes expressing such antibodies) and humanized antibody with complementarity determining regions of an antibody according to the invention may be made, for example in accordance with the methods disclosed in EP-A-0239400 (Winter).

The present invention further provides compositions comprising the antibody or fragment thereof of the invention together with a carrier or diluent. Such compositions include pharmaceutical compositions in which case the carrier or diluent will be pharmaceutically acceptable.

Polypeptides of the invention can be present in compositions together with a carrier or diluent. These compositions include pharmaceutical compositions where the carrier or diluent will be pharmaceutically acceptable.

Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

Polypeptides according to the invention, antibodies or fragments thereof to polypeptides according to the invention and the above-mentioned compositions may be used for the treatment, regulation or diagnosis of conditions, including proliferative diseases, in a mammal including man. Such conditions include those associated with abnormal (eg at an unusually high or low level) and/or aberrant (eg due to a mutation in the gene sequence) expression of one or more transcription factors such as the DP or E2F proteins or related family members. The conditions also include those which are brought about by abnormal expression of a gene whose gene product is regulated by the protein of FIG. 1A. Treatment or regulation of conditions with the above-mentioned peptides, antibodies, fragments thereof and compositions etc. will usually involve administering to a recipient in need of such treatment an effective amount of a polypeptide, antibody, fragment thereof or composition, as appropriate.

One group of preferred polypeptides according to the invention are those which are based upon the region of amino acids 384–413 of FIG. 1A. This region of the protein is capable of binding to p107.

The invention also provides, and fragments thereof, targeted to this region in order to inhibit the activation of transcription factors via the disruption of the formation of the E2F-4-DP protein complex.

The present invention further provides a method of performing an immunoassay for detecting the presence or absence of a polypeptide of the invention in a sample, the method comprising:

(a) providing an antibody according to the invention;
(b) incubating the sample with the antibody under conditions that allow for the formation of an antibody-antigen complex; and
(c) detecting, if present, the antibody-antigen complex.

In another aspect, the invention provides a novel assay for identifying putative chemotherapeutic agents for the treatment of proliferative or viral disease which comprises bringing into contact a DP protein or a derivative thereof, a polypeptide of the invention and a putative chemotherapeutic agent, and measuring the degree of inhibition of formation of the DP/E2F-4 protein complex caused by the agent. It may not be necessary to use complete DP-1 and/or E2F-4 protein in the assay, as long as sufficient of each protein is provided such that under the conditions of the assay in the absence of agent, they form a heterodimer.

The cloning and sequencing of DP-1 (and E2F 1,2 and 3) are known in the art and methods for the recombinant expression and preparation of antibodies to DP-1 can be found in WO-A-94/10307.

Thus, the invention provides a screening method for identifying putative chemotherapeutic agents for the treatment of proliferative disease which comprises:

(A) bringing into contact:
  (i) a DP polypeptide;
  (ii) a polypeptide of the first aspect, and
  (iii) a putative chemotherapeutic agent;
under conditions in which the components (i) and (ii) in the absence of (iii) form a complex; and
(B) measuring the extent to which component (iii) is able to disrupt said complex. In the assay, any one or more of the three components may be labelled, eg with a radioactive or colorimetric label, to allow measurement of the result of the assay. Putative chemotherapeutic agents include peptides of the invention.

Variants, homologues and fragments of DP proteins are defined in a corresponding manner to the variants, homologues and fragments of the E2F-4 protein.

The complex of (i) and (ii) may be measured, for example, by its ability to bind an E2F DNA binding site in vivo. Alternatively, the assay may be an in vivo assay in which the ability of the complex to activate a promoter comprising an E2F binding site linked to a reporter gene is measured. The in vivo assay may be performed for example by reference to the examples which show such an assay in yeast, insect, amphibian or mammalian cells.

Candidate therapeutic agents which may be measured by the assay include fragments of 10 or more amino acids of
(a) the protein of FIG. 1A;
(b) an allelic variant or species homologue thereof; or
(c) a protein at least 70% homologous to (a).

Vectors carrying a polynucleotide according to the invention or a nucleic acid encoding a polypeptide according to the invention may be used in a method of gene therapy. Such gene therapy may be used to treat uncontrolled proliferation of cells, for example a tumour cell. Methods of gene therapy include delivering to a cell in a patient in need of treatment an effective amount of a vector capable of expressing in the cell either an antisense polynucleotide of the invention in order to inhibit or reduce the translation of E2F-4 mRNA into E2F-4 protein or a polypeptide which interfered with the binding of E2F-4 to a DP protein or a related family member.

The vector is suitably a viral vector. The viral vector may be any suitable vector available in the art for targeting tumour cells. For example, Huber et al (Proc. Natl. Acac. Sci. USA (1991) 88, 8039) report the use of amphotrophic retroviruses for the transformation of hepatoma, breast, colon or skin cells. Culver et al (Science (1992) 256; 1550–1552) also describe the use of retroviral vectors in virus-directed enzyme prodrug therapy, as do Ram et al (Cancer Research (1993) 53; 83–88). Englehardt et al (Nature Genetics (1993) 4; 27–34 describe the use of adenovirus based vectors in the delivery of the cystic fibrosis transmembrane conductance product (CFTR) into cells.

The invention contemplates a number of assays. Broadly, these can be classified as follows:
1. Conducting an assay to find an inhibitor of E2F-4 trans-activation (that is to say, inhibition of activation of transcription). This inhibitor may therefore inhibit binding of E2F-4 to DNA (usually at the E2F binding site). Potentially suitable inhibitors are proteins, and may have a similar or same effect as p107. Thus suitable inhibitory molecules may comprise fragments, mutants, allelic variants, or species homologues of p107 in the same manner as defined for proteins of the first aspect.
2. Assaying for inhibitors of (hetero)dimerisation. Such inhibitors may prevent dimerisation of E2F-4 (or a polypeptide of the first aspect) with a complexor, for example a DP protein, such as DP-1. Of course the inhibitor can be a fragment, mutant, allelic variant or species homologue of a DP protein in a similar manner as defined for the proteins of the first aspect.
3. A third category of assay is to find inhibitors of phosphorylation. It is thought that E2F-4 (and other proteins of the first aspect) might be activated by phosphorylation. Therefore, an inhibitor of phosphorylation is likely to inhibit E2F-4 trans-activation properties (and may, therefore, ultimately have the same effect as the inhibitors found in either of the two previous assays). Phosphorylation is by cdk's and so an inhibitor of his phosphorylation is one that is contemplated by such assays.

The invention contemplates a number of therapeutic uses. For example, gene therapy using a nucleic acid a sequence that is antisense to E2F-4. Molecules that can bind to a DP-1 protein and thereby form an inactive complex with the DP protein are additionally contemplated. Suitable molecules include those of the first aspect apart from E2F-4 itself. Such molecules may be mutants of E2F-4, and are often referred to as dominant negative molecules in the art.

The invention contemplates the treatment or prophylaxis of diseases that are based on the uncontrollable proliferation of cells, or where uncontrolled proliferation is an important or essential pathological aspect of the disease. This includes cancer, viral disease, self proliferation itself as well as auto immune diseases such psoriasis. One may also wish to temporarily inhibit the growth of dividing cells, for example hematopoietic stem cells and/or bone marrow cells. In these aspects one is generally seeking to prevent, inhibit or interfere with the activity of E2F-4.

In contrast some diseases and conditions can be treated by increasing E2F-4 expression, for example by promoting or inducing overexpression. This preferably results in apoptosis, sometimes known as programmed cell death. Overexpression of the E2F-4 protein can result in death of the cell, and therefore this aspect can also be used in the treatment of cancer. One aim is therefore to increase the activity of E2F-4. Similar uses are known for E2F-1 (Qin et al, PNAS USA 91 (in press)).

It should be borne in mind that the E2F-4 gene might be mutated in tumour cells. In that event, the mutated gene could be used in diagnosis of a condition resulting from the mutation. It also lends itself to treatment via the mutated genes.

The following examples describe the isolation and characterization of the novel protein and DNA of the invention from a human source. However, other e.g. mammalian sources are within the scope of the present invention and the other e.g. mammalian homologues of the protein may be isolated in an analogous manner.

The invention will now be described, by way of example, with reference to the accompanying Examples which should not be construed as being limited.

EXAMPLE 1

The E2F gene family encodes a number of closely related transcription factors that control gene expression during the cell division cycle. E2 F sites have been found in a number of genes whose expression is tightly regulated during the cell cycle (for review, see Nevins 1992; Farnham et al, 1993). Importantly, in a number of cases, it has been shown that mutation of the E2F-binding sites in the promoters of these genes leads to a loss of cell-cycle regulated expression (Farnham et al, 1993; Larn and Watson 1993). Complexes have been found between E2F and the retinoblastoma protein (pRb), E2F and the pRb-related p107, and E2F and a third member of the pRb gene family, p130. These three complexes show a different pattern of appearance during the cell cycle. Complexes between E2F and pRb are found mostly in the $G_1$ phase of the cell cycle, but some E2F/pRb complexes persist during S phase. The complexes between E2F and p107 show a more complex patter of appearance during the cell cycle. In $G_1$, DNA-binding complexes have been observed that contain E2F, p107, cyclin E, and cyclin-dependent kinases (dck), cdk2. In S phase cyclin E is no longer found in these complexes, but cyclin A is found associated with E2F, p107 and cdk2 (Lees et al 1992; Shirodkar et al, 1992). The function of these cyclin/cdk complexes in the E2F/p107 complex remains obscure as yet. In addition, complexes have been observed between E2F and p103 primarily in quiescent cells (Cobrinik et al, 1993). E2F/p130 complexes disappear quickly when cells emerge from quiescence and enter into the cell cycle.

The activity of E2F is tightly regulated by association with proteins of the pRb gene family. Two findings were critical for our understanding of the mechanism by which pRb regulates E2F activity. First, the demonstration that pRb can inhibit trans-activation by E2F showed that proteins of the pRb gene family act as negative regulators of E2F activity (Chellappan et al, 1991; Hamel et al 1992; Hiebert et al, 1992; Weintraub et al; 1992, Helin et al 1993). Second, the demonstration that E2F binds preferentially to hypophosphorylated pRb suggested that complex formation between pRb and E2F is regulated by phosphorylation of pRb (Buchkovich et al, 1989; Chen et al, 1989; DeCaprio et al, 1989). Since pRb can be phosphorylated by cyclin E and the D-type cyclins, when in complex with their respective cdk, these cyclin/cdk complexes are through to release E2F from pRb by phosphorylaating pRb. Recently, a second cyclin/cdk complex was shown to act as a negative regulator of E2F activity. Cyclin A can bind directly to E2F-1 and inhibit DNA binding by E2F-1 (Krek et al, 1994) As cyclins D and E are present primarily in late G, and cyclin A primarily in S phase, E2F-1 activity is likely to increase in late G, and decline in S phase when cyclin A is synthesized. It has been shown that p107, like pRb, can inhibit E2F-dependent gene expression (Schwarz et al, 1993; Zamanian and La Thangue 1993; Zhu et al. 1993). However, very little is known bout the regulation of the E2F activity that interacts with p107.

E2F DNA-binding activity consist of heterodimeric complex of two molecules: an E2F polypeptide and dimerization partner named DP-1, cDNAs encoding E2F-1 and DP-1 have been isolated by molecular cloning (Helin et al. 1992; Kaelin et al. 1992; Girling et al. 1993; Huber et al. 1993). Recently the complexity of this intricate network of interacting proteins (Ivey-Hoyle et al. 1993; Lees et al. 1993). E2F-1, E2F-2 and E2F-3 associate in vivo only with pRb and not with the related p107. The presence of E2F activity associated with p107 (Cao et al. 1992; Lees et al. 1992, Schirodkar et al., 1992) would indicate that the family of E2F-like polypeptides is even larger and includes additional members that have the ability to associate with p107. Consistent with this hypothesis, it has been shown that p107-associated E2F polypeptides are similar, but distinct from pRb-associated E2F polypeptides (Dyson et al. 1993). We report here the cloning of a novel member of the E2F gene family, E2F-4, that interacts with p107 in vivo. E2F-4 can promote cell-cycle progression and can act as an oncogene when overexpressed in primary fibroblasts.

Results

Isolation of cDNA clones encoding E2F-4

To isolate cDNAs encoding proteins that interact with p107, we screened a day-16 whole mouse embryo cDNA expression library with a $^{32}$P-labelled p107 protein probe. Three independent phage were isolated whose encodes fusion protein bound to p107. Partial DNA sequence analysis revealed that all three were derived from the same gene. The shortest clone had a cDNA insert of 800 bp and contained an open reading frame of only 31 amino acids. These 31 amino acids showed significant homology (15 of 31 identities) to the pRb-binding domain E2F-1. The longer cDNA clones showed additional homology to the three known E2Fs. We thus named the protein encode by this novel CDNA E2F-4. The partial mouse E2F-4 cDNA clones were then used to obtain longer mouse cDNAs and to isolate a human E2F-4 cDNA. Despite extensive efforts, we were unable to obtain the extreme 5' end of the human E2F-4 cDNA. We did, however, obtain a full length mouse E2F-4 cDNA. Comparision of the 5' ends of the mouse and human E2F-4 cDNAs indicated that the human cDNA only lacked the first 16 codons of E2F-4. These 16 amino acids, however, are fully conserved between mouse and human E2F-4 (Ginsbery et al., Genes & Development, Nov. 15, 1994). Translation of the human E2F-4 cDNA (including the first 16 amino acids derived from mouse E2F-4) yields a 413 amino-acid protein with a predicted molecular mass of 44 kD.

FIG. 1A shows the E2F-4 cDNA sequence and the deduced amino acid sequence. E2F-4 E2F-1 share three regions of homology (FIG. 1B). The overall similarity between the two proteins is 63% (41% identity). A striking difference between E2F-4 and E2F-1 is that E2F-1 has an additional 100 amino acids amino-terminal of the DNA-binding domain. This region of E2F-1 contains a cyclin A-binding site (amino acide residues 67–108; Krek et al., 1994). The first region of homology is from amino acids 10–82 of E2F-4 and 120–190 of E2F-1 (similarity 71%), which coincides with the DNA binding region of E2F-1 (Helin et al. 1993b). E2F-1 can only bind DNA in a heterodimeric complex with DP-1. The region required for DP-1 interaction is located downstream of the DNA-binding domain (amino acids 191–284). The similarity between E2F-4 and E2F-1 in this region is −64%. E2F-4 and E2F-1 diverge in the carboxyl terminus. Downstream of amino acid 194 of E2F-4 and 297 of E2F-1 there is a region with almost no sequence conservation. In this region, E2F-4 contains a remarkable stretch of 12 consecutive serines. Although E2 F-1 does not contain this stretch of serines, it does contain a region that is serine-rich. The function significance of this repeat in E2F-4 is presently unknown. The last segment of homology is located at the extreme carboxyl terminus of the two proteins. This region of homology corresponds to the region of E2F-1 that is involved in binding pRb (Helin et a l., 1992). Since the first E2F04 cDNA that we isolated with the p107 protein probed encoded only the last 31 amino acids of E2F-4, it is likely that this region, like its counterpart in E2F-1 that is sufficient for pRb binding, is sufficient for binding to p107. In this region, 15 of the 31 residues are identical between E2 F-4 and E2F-1.

To analyze the pattern of expression of E2F-4, a partial mouse E2F-4 cDNA was used to probe a Northern blot containing poly(A)' RNA from various tissues of the mouse. At high stringency, a single transcript of 2.1 kb was detected. The expression was high in kidney and thymus and relatively low in lung, brain, spleen, and testis (data not shown).

E2F-4 requires DP-1 for DNA binding

Efficient sequene-specific DNA binding by E2F-1 requires heterodimerization with a second protein named DP-1 (Helin et al. 1993b; Krek et al., 1993). To investigate whether E2F-4 can function like the other members of the E2F gene family, we investigated whether E2F-4 was able to bind an E2 F DNA consensus site, and whether DP-1 was required for DNA binding by E2F-4. We transfected U2OS osteosarcoma cells with DP-1 and E2F-4 expression vectors separately or together. After 2 days, gel shift extracts were made from the transfected cells, and these extracts were incubated with a $^{32}$P labelled oligonucleotide that specifies a consensus E2F site. DNA-protein complexes were then resolved on an acrylamide gel and detected by autoradiography.

It was found that transfection of U2-OS cells with DP-1 alone did not lead to increase in E2 F DNA binding activity. Tranfection of E2F-4 expression vector alone, however, yielded a clearly detectable increase in E2F activity. The most striking increase was seen when E2F-4 and DP-1 expression vectors were introduced simultaneously in the osteosarcoma cells. These results show that E2F-4 can bind to a consensus E2F site and that binding is enhanced in the presence of DP-1.

E2F-4 and DP-1are synergistic in the activation of an E2F site reporter.

Next we investigated whether E2F-4 has the ability to activate the transcription of a CAT reporter gene that was linked to a core promoter and four upstream E2F sites. We cotransfected C33A cervical carcinoma cells with increasing amounts of E2F-4 (FIG. 2A) or DP-1 expression vectors (FIG. 2B) and the CAT reporter plasmid. When transfected alone, E2F-4 was unable to activate transcription of the CAT reporter. In contrast, expression of DP-1 led to a clearly detectable increase in the activity of the reporter gene. When E2F-4 and DP-1 were cotransfected, a strong increase in transcriptional activity was observed. The activation by E2F-4 and DP-1 together was more that the sum of either plasmid alone, indicating that E2F-4and DP-1 are cooperative in trans-activation. The cotransfected of E2F-4 and DP-1 with a reporter plasmid containing a mutant E2F site did not result in increased activation of the reporter (data not shown). Together, these experiment demonstrate that E2F-4 is able to activate transcription from a promoter containing E2 F DNA-binding sites in the presence of DP-1.

p107 Inhibits E2F-4 Trans-activation

Transcriptional activation by E2F-1 can be suppressed by pRb, because the pRb-binding site of E2F-1 and the trans-activation domain overlap. Since E2F-4 was isolated with p107 protein probe, we studies, the effect of p107 on E2F-4 trans-activation. C33A cervical carcinoma cells were cotransfected with E2F-4 and DP-1 expression vectors and the E2 F-site containing CAT reporter plasmid in the presence of increasing amount of p107 expression vector. FIG. 4 shows that p107 can efficiently suppress E2F-4 trans-activation. Maximal inhibition was already observed with 200 mg of p107 expression vector. As a control we used the p107 mutant, p107DE, that lacks most of the pocket region of p107 (Zhu et al, 1993). Cotransfected of 1 $\mu$g of pCMVp107DE did not significantly affect E2F-4 trans-activation (FIG.3). When pRb was expressed, a decrease in E2F-4 mediated trans-activation was observed, although to a lesser extent than with p107. Inhibition of E2F-mediated trans-activation transfection of either p107 or pRb has been observed previously (Zamanian and La Thangue 1993; Zhu et al 1993), indicating that both pocket proteins are able to associate with endogenous E2F's when transiently overexpressed. These experiments, however, show that trans-activation by E2F-4can be suppressed by overexpression of wild type p107 or pRb and not by a mutant form of p107 protein lack growth-inhibitory activity (Zhu et al, 1993).

E2F-4 specifically interacts with p107 in vivo

In nontransfected cells E2F-1 interacts only with pRb and now the p107 (Dyson et al, 1993; Lees et al, 1993). However, when E2F-1 and p107 are transiently transfected an interaction can be observed(R. L. Beijersbergen and R. Bernards, unpubl.). This indicates that overexpression of these proteins may lead to interaction that are not observed under physiological conditions. E2F-4 wad identified by virtue of its ability to bind p107 in vitro. the date in FIG. 3 suggest that E2F-4 can interact with p107 and pRb in transiently transfected cells, but they did not show that these interaction also take place under physiological conditions. To address whether E2F-4 interacts with p107 and/or pRb in nontransfected cells. we generated E2F-4-specific polyclonal antiserum and used this in a sequential immunoprecipitatin experiment. ML-1 leukemia cells were metabolically labeled with [$^{32}$P]orthophosphate. Nonionic detergent lysates were prepared and subjected to immonumoprecipitatin with either p107-specific monoclonal antibody or pRb-specific antibody. Proteins that were coimmunoprecipitated with pRb and 107 were then released by heating in SDS-containing buffer, diluted and reimmunoprecipitaed with polyclonal E2F-4 antiserum, E2F-1 specific monoclonal antibody, or nonimmune control serum. Immunde complexes were separated on 7.5% SDS-polyacrylamide gels, and protein was detected by autoradiography. Consistent with the data of others (Dyson Et al, 1993; Lees et al, 1993) mAb E2F-1 recognized a single protein species that is present in the anti-pRb immunoprecipitate but not in the anti-p107 immunoprecipitate. Conversely, the E2F-4 antiserum clearly detected two closely migrating protein species that were present in the p107 immunoprecipitate. A very faint signal was detected when the E2F-4 antiserum was used to reimmunoprecipitate proteins associated with pRb. This could indicate that the E2F-4 may be bound to pRb.

We generated monoclonal antibodies that specifically recognize E2F-4 and not E2F-1, which recognize the same bands as detected by the polyclonal E2F-4 serum in ML-1 cells, HeLa cells and BJAB cells (data not shown). Taken together, these data strongly suggest that E2F-4 interact preferentially with p107, rather than with pRb.

s E2F-4 is a phosphoprotein

The E2F-4 monoclonal antibodies recognize a $^{32}$P-labelled protein in a p107 immunoprecipitate indicating that E2F-4 is phosphorylated in vivo. The finding that the E2F-4 antibodies recognized multiple closely migrating protein species could indicate that different proteins are recognized by the same antibody or that E2F-4 protein is subject to post-translational modifications that result in altered mobility in an SDS gel. To further investigate the nature of the different E2F-4 protein species that were present in p107 immunoprecipitates, we labeled ML-1 cells with [$^{35}$S]-methionine. mAb RK13 recognizes three protein species in a p107 immunoprecipitate (data not shown). The same pattern of bands was also detected when U2-OS cells were 10 mg of an E2F-4 expression vector indicating that the expression vector encodes the full-length E2F-4protein. to investigate whether these protein species were all derived from the same protein by differential phosphyorlation, we performed the following experiment. U2-OS cells were transfected with 10 $\mu$g of E2F-4; DP-1, and p107 expression vectors, labelled with [$^{35}$S]methionine, and immunoprecitated under low stringency conditions with p107 antibody. The p107 immunoprecipitate was treated in the presence or absence of calf intestine phosphate, and p107 associated proteins were reimmunoprecipitated with mAb E2F-4. It was found that following phosphatase treatment the three protein species that bind to p107 and are recognized by mAb RK13 were reduced to mostly a single fast migrating protein species, although some slower migrating species remain. Taken together, our data suggest that E2F-4 is a phosphoprotein and that the different E2F-4 protein species arise by differential phosphorylation of E2F-4.

Association of p107 with E2F-4 requires dimerisation with DP-1

To investigate whether E2F-4 requires DP-1 for interaction with p107, we transfected U2-OS cells with p107 and E2F-4 in the absence or presence of an hemagglutinin (A) epitope-tagged DP-1 expression vector. Transfected cells were labelled with [$^{32}$P]orthophosphate and after 40 hours cell lysates were immunoprecipitated at low stringency with p107 antibody to allow coimmunoprecipitation of p107-associated proteins. The E2F-4 and DP-1 proteins wree equally expressed in all transfections (data not shown). The anti-p107 immunoprecipitates were then boiled in 2% SDA and 15mM DTT to release assocaiatedproteins and release proteins were reimmunoprecipitated with the anti-E2F-4 mAb RK13 or with mAb 12CA5 directed against the HA-tagged DP-1. The transfection of p107 with DP-1 did not result in complex formation between these two proteins. The same result was obtained when p107 was cotransfected with E2F-4. In contrast, in cells transfected with all three expression vectors, p107, E2F-4 and DP-1 both E2F-4 and DP-1 were found in complex with p107.

Stimulation of Cell Proliferation by E2F-4/DP-1 Dimer

A number of cellular genes whose protein products are required for DNA synthesis contain E2F sites in their promoters (Nevins 1992). Transcriptional activation of these genes by E2F is believed to be an important and, in most cases, essential step in the controlled expression of these genes during the cell cycle. It is expected, therefore, that deregulated expression of active E2F would stimulate cell proliferation. Consistent with this, it has been shown that E2F-1 can stimulate quiescent cells to initiate DNA synthesis (Johnson et al, 1993).

In this study we investigated the growth-promoting effects of E2F-4 and its dimerization partner DP-1 in cycling cells. Osteosarcoma cell line SaoS-2 was transiently transfected with DP-1 or E2F-4 or cotransfected with E2F-4 and DP-1 expression vectors. Three days later the cells were harvested and processed for flow cytometry analysis to determine the proliferation status of the population. Transfected cells were identified by the cotransfected cell surface marker CD20 and analyzed in comparison to the control vector-transfected cells (Zhu et al 1993). Table 1 shows that the overexpression of DP-1 stimulated cell-cycle progression of the transfected population, decreasing the $G_1$ population and increasing the S-phase population at the same time by almost 20%. Overexpression of E2F-4 alone also resulted in an increase of S-phase cells, although to a smaller extent. Overexpression of E2F-4 together with DP-1 exhibited the most dramatic effect by decreasing the $G_1$ population and increasing the $G_2$+M-phase population as indicated in three independent experiments. These results indicate either that overexpression of E2F-4 DP-1 promote entry into S phase or delay exit from later stages of the cell cycle. Since E2F-4 can act as a dominant oncogene in transformation of primary rodent fibroblast we favour the explanation that E2F-4 promotes cell-cycle progression rather inhibiting exit from S phase and $G_2$/M phase of the cell cycle.

TABLE 1

Overexpression of E2F-4/DP-1 Stimulates Cell Proliferation

|  | Experiment | Phase $G_0G_1$ | Phase S | Phase $G_2$/M |
| --- | --- | --- | --- | --- |
| pCMV | 1 | 51.1 | 31.7 | 17.2 |
|  | 2 | 44.6 | 33.3 | 22.1 |
|  | 3 | 55.3 | 23.9 | 20.7 |
| pCMV-DP-1 | 1 | 33.4 | 48.5 | 18.1 |
| pCMV-E2F-4 | 1 | 41.5 | 44.1 | 14.4 |
| pCMV-E2F-4 + | 1 | 28.5 | 43.1 | 28.4 |
| pCMV-DP-1 | 2 | 25.4 | 40.6 | 34.0 |
|  | 3 | 30.3 | 40.6 | 29.1 |

SaoS-2 cells were transfected with pCMV-CD20 CD 20 cell surface protein in combination with expression vectors pCMV, pCMV-DP-1, pCMV-E2F-4, of pCMV-E2F-4 together with pCMV-DP-1. Transfected cells were analyzed by FACS and cell cycle profiles of CS20-positive cells was determined. The percentage of cells in $G_0/G_1$, S, and $G_2$/M phase are depicted.

Overexpression of E2F-4 and DP-1 together with ras causes transformation

The effect of E2F-4 on cell-cycle progression suggests a role for E2F-4 in normal cell-cycle control. If this is the case, overexpression of E2F-4 might result in deregulated growth control. Proteins that promote transition from $G_1$ to S phase of the cell cycle may have immortalizing activity on primary cultures of fibroblasts. For example, both adenovirus E1A and c-Myc promote S phase entry (Heikkila et al 1987; Moran and Mathews 1987; Eilers et al, 1991) and have immortalizing activity when introduced in primary rat embryo fibroblast (REF) cultures (Land et al, 1983; Ruley 1983).

To study the effect of E2F-4 on primary cultures of REFs, we transfected REFs with E2F-4, DP-1 expression vectors alone, or cotransfected with E2 F-4 and DP-1. In all experiments a plasmid encoding a mutant Ha-ras onogene was cotransfected to obtain full oncogenic transformation (Land et al, 1983). Since both the E2F and DP-1 expression vectors contain a neomycin resistance gene, colonies of transformed cells could be selected in the presence of G418. After 4 weeks G418-resistant colonies were detected only in the E2F-4, DP-1-, and ras-transfected cells and not in the E2 F-4 plus ras- or DP-1- plus ras- transfected cells. The morphology of two colonies of REFs, E4R1 and E4R2, transfected with E2R-4, DP-1 and ras, were compared with the primary REF culture. Both transfectants had a transformed morphology. Consistent with their transformed morphology both transfectants were able to form colonies in soft agar and gave rise to tumors with short latency periods when $5 \times 10^n$ cells were injected in nude mice (data not shown).

The expression of E2F-4 and DP-1 in the transformed REF. cell lines was measured in two independent assays. First, the REF cell lines were labelled with [$^{32}$P] orthophosphate and subjected to immunoprecipitation with mAb 12CA5 directed against the HA-tagged DP-1. Immune complexes were separated on 7.5% SDS-polyarcylamide gels and detected by autoradiography. Equal amounts of $^{32}$P-labelled cell lysates were used for immunoprecipitation. it was found that both E2F-4 plus DP-1transfected REF cell lines, E4R1 and E4R2, but not control adenovirus 5transformed REFs, expressed the 55kD HA-tagged DP-1 protein. In the former two lines, mAb 12CA5also immunoprecipitated a 6--kD protein that could be reimmunoprecipitated with mAb E2F-4. These data indicate that the immortalized REF cell lines express both DP-1 and e2F-4.

To further analyze the E2F DNA-binding activity in these REFs, we made nuclear extracts of E4R2 and adenovirus 5-transformed REFs and used these in a gel retardation assay. The E2F-4 transfectant E4R2 showed a dramatic increase in total amount of E2F DNA-binding activity, which was completely supershifted by the addition of the E2F-4 antiserum (data not shown). Furthermore, most of the E2F activity in the E4R2 was free E2F, whereas in the adenirus-transfected line only slower migrating complexes were observed that were not affected by the E2F-4 antiserum. We conclude that overexpression of E2F-4 DP-1 with an increased E2F-4 DNA-binding activity in REFs, in combination with an activated ras oncogene, results in the generation of transformed cell lines that have oncogenic activity.

Discussion

We have isolated a forth member of the E2F gene family. E2F-4 differs from the three known E2Fs in that E2F-4 associates in vivo preferentially with the pRb-related p1-7 and only weakly, if at all, with pRb itself. In contrast, E2 F-1, E2F-2, and E2F-3 interact only with pRb and not with the 107. In spite of this important difference, there are a number of striking similarities between the pRb E2Fs and the p107 E2F described here. First, there is significant structural homology between these two classes of proteins in the DNA-binding domain and the DP-1 dimerization domain. Consistent with this, we found that E2 F-4 can activate transcription of a promoter that harbors consensus E2F DNA-binding sites and that E2F-4 requires DP-1 for efficient DNA binding. Transcriptional activation by E2F-4 can be repressed by overexpression of p107. These results indicate that the E2F-4/p107 complex is transcriptionally inactive. Similarly, the pRb-associated E2Fs are also transcriptionally inactive when complexed by pRb. The finding that E2F-4 can bind a consensus E2F-binding site in cooperation with DP-1 does not rule out the possibility that in vivo E2F-4 will bind to a difference subset of E2 F site-containing promoters that the pRb/E2Fs. Regulation by the various pocket proteins may lead to activation of E2Fs at distinct points in the cell cycle and may therefore result in the sequential activation of promoters with a particular E2F site. The recent finding that the thymidine kinase and b-myb promoters carry E2F sites that preferentially bind E2F/p107 complexes supports the notion that pRb/E2Fs and p107/E2Fs differ subtly in DNA-binding specificity (Lam and Watson 1993; Li et al, 1993a).

Overexpression of p107 leads to a $G_1$ arrest in a number of cell types (Zhu et al, 1993). Since the pocket region of p107 is required for growth-suppressive activity, it is likely that p107 inhibits cell-cycle progression by binding to a number of cellular proteins that are involved in promoting progression from $G_1$ to S phase of the cell cycle. We and others have recently shown that the c-Myc oncoprotein can form a specfic complex with p107 in vivo (Beijersbergen et al, 1994; Gu et al, 1994). Importantly, binding of p107 to the c-Myc trans-activation domain resulted in a dramatic inhibition of c-Myc trans-activation. Since high level expression of c-Myc was able to override a p107-induced cell-cycle block, it is likely that p107 inhibits cell-cycle progression, at least in part, by binding to and inactivating the c-Myc protein (Beijersbergen et al, 1994). Our present data add E2F-4 to the short list of p107 interacting cellular proteins, and a striking similarity between c-Myc and E2F-4 becomes apparent from the present study. First, both c-Myc and E2F-4 appear to have a trans-activation domain that can bind p107, resulting in inhibition of trans-activation. Furthermore, our data indicate that E2F-4, like c-Myc, may promote progression for $G_1$ to S phase of the cell cycle (Table 1; Heikkila et al, 1987; Eilers et al, 1991). This interpretation is substantiated by the observation that E2F-4, like c-Myc, can cooperate with an activated ras oncogene in the transformation of REF cultures. Therefore, it will be worthwhile to study the possible involvement of E2F-4 in human cancer.

Although p107 can inhibit the activity of cell cycle regulatory proteins such as c-Myc and E2F-4, mutant forms of p107 do not appear to occur in human cancers. One possibility is that p107 is functionally redundant. The p107-related protein p130, which was recently isolated by molecular cloning, is a candidate for a protein having p107-like activity. p130 is structurally more related to p107 than to pRb (Hannon et al, 1993; Li et al, 1993b), p130 also has been observed in complexes with E2F DNA-binding activity and higher order complexes between p130 and cyclin E/cdk2 and cyclin A/cdk2 have also been observed (Cobrinik et al, 1993). However, p130/E2F complexes occurred in different stages of the cell cycle as compared with the p107/E2F complexes.

An important question that remains to be resolved concerns the regulation of E2F-4 activity in the cell cycle. From the study of the E2F-1-pRb interaction it is clear that not only phosphorylation of pRb but probably also of E2F-1 and DP-1 by cdks is important in controlling activity (Krek et al, 1994). In contrast, very little is known about the regulation of p107 by phosphorylation. The cdks play a key role in regulation p107/E2F complex formation is, however, quite likely.

Lees et al, (1992) have detected cell-cycle regulated complex formation amount E2F, p107, and cyclin E/cdk2 in the $G_1$ phase of the cell cycle. In S phase, a complex of E2F, p107, and cyclin A/cdk2 was detected. The appearance of the different cyclin/cdk complexes in the E2 F/p107 complex follows the kinetics of the synthesis of these cyclins. The role of these two cyclin/cdk complexes in controlling the E2F/p107 interaction is presently not known. It is possible that these kinases phosphorylate p107 and/or E2F-4. Our finding that E2F-4 is a phosphoprotein is consistent with a role for cyclin/cdk complexes in controlling E2 F-4 is a phosphoprotein is consistent with a role for cyclin/ckd complexes in controlling E2F-4 activity. Whatever the targets of these cyclin/cdk complexes may be, their presence does not appear to lead to the dissociation of the p107/E2F complex. Since complexes between E2F and p107 are found throughout the cell cycle, it is not obvious when p107-interacting E2Fs are free to activate transcription of their target genes. We are currently studying the effect of the various cyclin/cdk complexes on E2F-4/p107 complex formation and the effect of these kinases on E2F-4 activity. The availability of the first p107 specific E2F should be a helpful tool in understanding the regulation of p107 by cdks and the differences between regulation of pRb and p107 by these kinases.

Material and Methods for Example 1
Screening of cDNA libraries with p107

The p107 protein probe used in the screening of cDNA expression libraries was GST-2TK-p107, containing the pocket region of human p107. The GST-1 TK vector contains a consensus phosphorylation site for protein kinase A (Blanar and Tutter 1992). GST-p107 fusion protein was made in *Escherichia coli*, purified and labelled in vitro with [$\gamma$-$^{32}$P]ATP as described to a sp. of >1×10$^8$ cpm/ $\mu$g of protein. A mouse embryo cDNA library in $\lambda$EX/lox (obtained from Novagen, Madison, Wis.) was screened with the p107 protein probe as described (Ayer et al. 1993). In a screening of 5×10$^5$ phages, 3 positive phages were The partial mouse E2F-4 cDNA was used to screen additional mouse and human cDNA libraries. The human E2F-4 cDNA described here was isolated from the T84 colon carcinoma library (obtained from Stratagene).

Plasmids pGST-E2F-4 was constructed by cloning a fragment of the human E2F-4 cDNA encoding amino acids 108–300 in pGEX3X. For transfection experiments the following plasmids were used: pCMV E2F-4 was constructed by linking the 5' end of mouse E2F-4 (encoding amino acids 1–16) to a fragment of the human E2F-4 cDNA encoding amino acids 17–413 at the conserved NaeI site in pRc/CMV (Invitrogen), pCMV-11A-DP-1 has been described (Helin et al, 1993b), pCMV-E2F-1 was generated by inserting the coding sequence of pSP72 RBAP-1 (Kaelin et al, 1992) in pRc/CMV. The plasmids pCMV-pRb, pCMV-p107, pCMV-p107DE were described previously (Zhu et al. 1993).

Cell lines

Human C35A, ML-1, and U2-OS were cultured in Dulbecco's modified Eagle medium (DMEM) with 10% fetal calf serum (FCS). REFs were isolated from 13 day-old rate embryos and cultured in DMEM in the presence of 10% FCS. Transfections were performed using the calcium phosphate precipitation technique (Van de Eb and Graham 1980). Stable transfectants were obtained after selection with 0.5 mg/ml of G418 for 4 weeks.

Immunological reagents To generate antibodies against E2F-4, a bacterial expression plasmid containing gluathione S-transferase (GST)-E2F-4 (amino acids 108–300) was generated. ST-E2F-4 protein was made in *E. coli*, purified over glutaathione-Sepharose™ beads, and used to immunise mice. After three rounds of immunization with GST-E2F-4, polyclonal serum was obtained. Monoclonal antibodies were prepared by fusion of splenocytes of immunized BALB/c mice to Sp$_2$O myeloma cells four days after the final boost. Positive tissue culture supernatants were identified in an ELISA. Supernatants of 19 different ELISA positive hybridoma cell lines were tested in immunoprecipitation. For the experiments described we used the polyclonal serum pc11 and the mAb RK13. Antibodies against p107 (SD2, SD4, SD9, SD6, SD15), pRb (XZ77 and C36) and against the HA epitope (12CA5) have been described previously) Hu et al, 1991; Zhu et al, 1993).

Metabolic labelling

Cells were incubated for 1 hr in phosphate free DMEM or methionine-free DMEM in the presence of 10% FCS, followed by an incubation in medium containing 5 mCi [$^{32}$P] orthophosphate or 250 µCi Trans [$^{32}$S]label for 4 hr.

Immunoprecipitations

Cells were lysed in ELB$^+$ buffer[containing 5 mM EDTA, 1mM DTT, 10 mM NaF, 10 mM sodium orthovanadate, 0.2 mM sodium pyrophosphate. 1 µg/ml chymostatin and aprotinin, and 1 mM phenylmethylsulphonyl fluoride (PMSF) and immunoprecipitated as described previously (Beijersbergen et al, 1994).

Phosphatase Treatment

Transiently transfected U2-OS cells were labelled with [$^{35}$S]methionine and precipitated with mAb 12CA5 as described. After the first immunoprecipitation, the precipitated proteins were washed three times in ELB$^+$ buffer followed by a wash with 1 ml of phosphatase buffer [50 mM Tris-HCI (pH 9.0), 5 mM MgCl$_2$ containing 1 mM PMSF, and 1 µg/ml of both chymostatin and aprotinin]. The immunoprecipitated proteins were split into two and resuspended in 50 µl of phosphatase buffer and incubated for 30 min at 30° C. in the absence or presence of 5 units of calf intestine alkaline phosphatase (Boehringer). Reactions were terminated by addition of 50 µl of 2 x releasing buffer (ELB$^+$ containing 4% SDS and 30 mM DTT) and boiled for 10 min. After this, protein A-Sepharose™ heads were removed by centrifugation and the supernatant diluted to 1 ml ELB buffer and precleared with protein A-Sepharose™ beads. The released proteins were then immunoprecipitated with mAb RK13. The immunoprecipitated proteins were collected by binding to protein A-Sepharose™ beads, boiled in SDS-containing buffer, separated on a 7.5% SDS-polyacrylamide gel, dried, and subjected to fluorography.

CAT Assays

C33A cells were transiently transfected with the expression vectors as indicated together with 2 µg of E2F$_4$ CAT (Helin et al., 1993b) 0.2 µg of RSV luciferase, and pRc/CMV to a total of 20 µg/10 cm composition plate. Cells were harvested 40 hr after transfection, and the transfected cells were resuspended in 100 µl of 0.1 M Tris-HCl (pH 8.0). The cells were freeze-thawed three times and centrifuged at 15,000 g, at 4° C. for 10 min. Supernatants were assayed for luciferase activity (Promega, Luciferase system) and CAT activity using the phase extraction assay (Seed and Sheen 1988).

Gel Retardation Assays

Transfected U2-OS cells were washed three times with PBS and the cells were collected to PBS. After centrifugation at 1000 g, the cells were resuspended in 100 µl of 5 x binding buffer [100 mM HEPES (pH 7.4), 0.5 M KCl, 5 mM MgCl$_2$, 0.5 mM EDTA, 35% glycerol, 5 mM NaF]. After one freeze-thaw step, the cells were kept on ice for 30 min. The extracts were centrifuged at 100,000 g for 30 min at 4° C. The supernatant was used in gel retardation assays.

Gel retardation assays for transiently transfected U2-OS cells were performed as described previously (Helin et al, 1993] with minor modifications. Ten micrograms of cell extract was used in 20 µl reactions containing 1 xbinding buffer and 1 µg of sonicated salmon sperm DNA. Reactions were incubated for 10 min at room temperature, after which 0.5 mg of $^{32}$P-labelled oligonucleotide containing the consensus E2F DNA-binding site (Santacruz) was added and the reaction was incubated for an additional 20 min at room temperature. The reaction products were separated on a 3.5% polyacrylamide gel in 0.25% TBE at 90V for 2.5 hr. The gel was then dried, and reaction products were visualized by autoradiography.

EXAMPLE 2

The orderly progression through the cell cycle is mediated by the sequential activation of several cyclin/cyclin-dependent kinase (cdk) complexes. These kinases phosphorylate a number of cellular substrates, amongst which is the product of the retinoblastoma gene, pRb. Phosphorylation of pRb in late G1 results in the release of the transcription factor E2F from pRb, resulting in the transcriptional activation of E2F responsive genes. This Example shows that phosphorylation of the pRb-related p107 is also cell cycle regulated. p107 is first phosphorylated at 8 hours following serum stimulation of quiescent fibroblasts, which coincides with an increase in cyclin D1 protein levels. Consistent with this, we show that a cyclin D1/cdk4 complex, but not a cyclin E/cdk2 complex, can phosphorylate p107 in vivo. Furthermore, phosphorylation of p107 can be abolished by the overexpression of a dominant negative form of cdk4. Phosphorylation of p107 results in the loss of the ability to associate with E2F-4. a transcription factor with growth promoting and oncogenic activity. A p107-induced cell cycle block can be released by cyclin D1/cdk4, but not by cyclin E/cdk2. These data indicate that the activity of p107 is regulated by phosphorylation through D-type cyclins.

The cell division cycle is mammalian cells is regulated by the cyclical activation of a number of kinases whose activity depends on their associated with a cyclin subunit (Sherr, 1993). In the G1 phase of cell cycle, cyclins D and E are expressed. D type cyclins are encoded by a family of three closely related genes, cyclin D1, D2 and D3, whereas only a single gene for E type cyclin has been isolated (Matsushime et al., 1991; Koff et al., 1991). Several lines of evidence indicate that D and E type cyclins are rate-limiting for passage through G1. Antibodies to cyclin D1 block S phase entry in several cell types (Baldin et al., 1993; Lukas et al., 1994) and over-expression of both cyclin D1 and E shortens G1 (Ohtsuho and Roberts, 1993; Quelle et al., 1993; Resnitzky et al., 1994; Wimmel et al., 1994). Since induction of cyclin D1 or E expression in serum-starved cells does not result in S phase entry, it appears that the expression of these cyclins necessary but not sufficient to progress through G1 into S phase (Resnitzky et al., 1994).

An important difference between cyclins D and E is that D type cyclins are implicated as a causal agent in cancer: cyclin D1 gene amplification has been found in breast cancer, esophageal carcinoma and squarmous cell carcinoma (Lammie et al., 1991, Jiang et al., 1992; Schuuring et al., 1992a, b). Furthermore, cyclin D1 is translocated in parathyroid adenomas and in centrocytric lymphomas (Withers et al. 1991; Rosenberg et al., 1991; Motokura et al., 1991; Seto et al., 1992). More recently, the product of the mts-1 tumor suppressor gene was identified as p16, a strong inhibitor of cyclin D1-associated kinase activity (Serrano et al., 1993; Kamb et al., 1994). Finally, in vitro, cyclin D1 can cooperate with other oncogenes to transform fibroblasts (Hinds, et al., 1994; Lovec et al., 1994) and in transgenic mice over-expression of cyclin D1 in breast epithelium results in breast cancer (Wang et al., 1994).

Because of the involvement of D type cyclins, and not of E type cyclins in the genesis of several types of human cancer, important functional differences are likely to exist between these two G1 cyclins. One such difference may be the kinetics of induction of D versus E type cyclins. Cyclin E is a "generic" cyclin in that its expression is induced in a cyclical fashion in the cell cycle, reaching maximal levels towards the end of G1 and cyclin E-associated kinase activity has been shown to peak at the G1/S transition (Koff et al., 1992; Dulic et al., 1992). In contrast, cyclin D1 appears to be induced most strongly following mitogen stimulation of quiescent cells (Matsushime et al., 1991, 1994; Won et al., 1992; Ajchenbaum et al., 1993; Sewing et al., 1993). Whether D1 cyclin is also expressed in a cyclical fashion in exponentially growing cells is controversial. Some have shown invariant expression of cyclin D1 during the cell cycle, whereas others have seen cell cycle-dependent variation in cyclin D1 levels (Matsushime et al., 1991; Baldin et al., 1993; Sewing et al., 1993; Lukas et al., 1994). Since several strong inhibitors of cyclin D1-associated kinase activity exist, an important question that has so far not been addressed is whether the cyclin D1-associated kinase activity varies during the cell cycle.

The product of the retinoblastoma gene, pRb, is a substrate for G1 cyclin/cdk complexes. Extracts from insect cells infected with recombinant baculoviruses that express either cyclin E and cdk2 or D type cyclins and cdk4 efficiently phosphorylate rRb in vitro (Ewen et al., 1993; Kato et al., 1993). In human osteosarcoma cells, expression of cyclin E, D2 and D3, but not of D1, resulted in hyperphosphorylation of pRb (Hinds et al., 1992; Ewen et al., 1993). Significantly, a pRb-induced cell cycle block could be released by ectopic expression of cyclin E, D2 and D3, but not effectively by cyclin D1 expression (Hinds et al., 1992; Ewen et al., 1993).

The retinoblastoma protein and the related p107 and p130 interact with several cellular polypeptides including E2F, a transcription factor that controls gene expression during the cell cycle (Cao et al., 1992; Cobrinik et al., 1993) E2F DNA binding activity consists of a heterodimeric complex containing an E2 F component complexed to a DP component (Bandara et al., 1993; Helin et al., 1993; Krek et al., 1993). The E2F component of the heterodimer is encoded by at least five closely related polypeptides, E2F-1, 2 and 3 associated in vivo only with pRb and not with the related p107 (Lees et al., 1993), E2F-4 in contrast seems to interact with p107 and p130, but not with pRb (Beijersbergen et al., 1994b; Ginsberg et al., 1994, Vairo et al., 1995, R. L. B. and R. B., unpublished data), whereas E2F-5 interacts only with p130 (M. Hijmans, et al., 1995). E2F binds preferentially to hypophosphorylated pRb suggesting that complex formation between pRb and E2F is regulated by phosphorylation of pRb by cyclin/cdk complexes (Buchkovich et al., 1989; DeCaprio et al., 1989; Chen et al. 1989; Chellappan et al., 1991). Hypophosphorylated pRb is found mostly in the G1 phase of cell cycle, whereas the hyperphosphorylated form of pRb is first observed at the G1 to S transition (Buchkovich et al., 1989; DeCaprio et al., 1989).

The complexes between E2F and p107 show a more complex pattern of appearance during the cell cycle. In late G1, DNA-binding complexes have been observed that contain E2F, p107, cyclin E and edk2. In S phase cyclin E is no longer found in these complexes, instead E2F is found associated with p107, cyclin A and cdk2 (Lees et al., 1992; Shirodkar et al., 1992). In spite of the presence of cyclin/cdk complexes in association with p107, very little is known about the regulation of p107 by the phosphorylation. In contrast to pRb, cell cycle regulated phosphorylation of p107 has not been observed. We show here that the growth inhibitory activity of p107 is subject to regulation by phosphorylation by cyclin/cdk complexes.

Results.

Effect of cyclin E on p107.

In late G1 phase of the cell cycle, p107 is found in a multi protein complex that contains E2 F DNA binding activity, cyclin E and cdk2 (Lees et al., 1992). To study the effect of cyclic E and its associated kinase cdk2 on the E2F/p107 complex, we used a transient transfection assay with E2F-4, We have shown recently that E2F-4 associates in vivo specifically with p107 and not with pRb. As a control, we studied the effect of cyclin E/cdk2 on the pRb/E2F-1 complex. We co-transfected a CAT reporter gene harboring upstream E2F sites together with either E2F-4 and DP-1 expression vectors on with E2F-1 and DP-1 expression vectors. FIG. 4A and B show the both the E2F-4/DP-1 and the E2F-1/DP-1 heterodimers efficiently activated the CAT reporter gene (tracks 3). As expected, co-transfection of p107 inhibited E2F-4 transactivation and pRb expression suppressed E2F-1 transactivation (tracks 5). When cyclin E/cdk2 and pRb expression vectors were co-transfected, a release of E2F-1 inhibition by pRb was observed, presumably as a result of phosphorylation of pRb by cyclin E/cdk2 (FIG. 4A, track 6) (Hinds et al., 1992, Ewen et al., 1993), Surprisingly, co-transfection of cyclin E/cdk2 with p107 failed to relieve p107 inhibition of E2F-4 (FIG. 4B, track 6). We conclude that cyclin E/cdk2 acts differently on pRb and p107 in that cyclin E/cdk2 can release pRb, but not p107 inhibition of E2F.

Effect of D type cyclins on p107

Next, we studied the effect of the cyclin D1 on p107. FIG. 5 shows that, in contrast cyclin E/cdk2, cyclin D1, together with its major catalytic partner cdk4, can release p107 inhibition of E2F-4 and pRb-inhibition of E2F-1 (FIG. 5A, B, compare tracks 4 and 7). The inactivation of p107 as an inhibitor of E2F-4 activity could be caused by several mechanisms. First, cyclin D1/cdk4 could phosphorylate p107, thereby releasing active E2F-4. An alternative mechanism of cyclin D1 action could be the direct binding of cyclin D1 to the pocket region of p107, since cyclin D1 shares a motif (LXCXE) with a number of viral transforming proteins that bind avidly to p107 and pRb through this motif (Dowdy et al., 1993). However, neither cyclin D1 alone nor cdk4 alone wire able to release p107 and pRb inhibition of E2F activity (FIG. 5A, B). This suggests that a cyclin D/cdk complex is required to release p107 inhibition of E2F-4.

To a study the kinase requirement of D type cyclins to inactivate p107, we co-transfected E2F-4 and p107 with other combinations of D type cyclins and cdks. To address the specificity of the kinase, we expressed cyclin D3, instead of cyclin D1, in combination with either cdk2 or cdk4. Both cdk2 and cdk4, when bound to cyclin D3, have significant kinase activity towards pRb, whereas cyclin D1 only forms an active complex with cdk4 (Ewen et al., 1993). FIG. 6 shows that although cyclin D1/cdk4 and cyclin D3/cdk4 effectively rescued E2F-4 inhibition by p107, no release of inhibition was observed with cyclin D3/cdk2. (FIG. 6, compare tracks 6, 8, and 9). These data indicate that not only the cyclin, but also the associated kinase contributes to the activity of the cyclin/cdk complex towards p107.

The data shown above are consistent with a model in which some, but not all, cyclin D/cdk complexes can phosphorylate and functionally inactive p107. To further study the molecule mechanism by which cyclin D1 and on p107, we used two mutants of cyclin D1. The first mutant, cyclin D1-GH carries a mutation in the LXCXE motif that is required for high affinity binding of cyclin D1 to pocket proteins. As a result, the GH mutant of cyclin D1 is defective for binding to pocket proteins (Dowdy et al., 1993; Hinds et al., 1994). The second mutant, cyclin D1-KE carries a mutation in the cyclin box, a domain that mediates association with cdks. The KE mutant is therefore unable to form a stable complex with cdk4 (hinds et al., 1994). FIG. 7 shows that the cyclin D1 GH mutant retained the ability to release E2F-4 from p107 inhibition, whereas the KE mutant was inactive in this assay. These data are consistent with the notion that cyclin D1/cdk4 phosphorylates p107 and do not support the hypothesis that cyclin D1 competes with E2F-4 for binding to the p107 pocket.

To further substantiate that phosphorylation is essential for the inactivation of p107, we used a dominant negative mutant of cdk4 (Van den Heuvel and Harlow, 1993). FIG. 18A shows that this kinase inactive edk4, in combination with cyclin D1, was not able to release the p107 inhibition of E2F-4, indicating that kinase activity of the cyclin D/cdk4 complex is essential for the release of the p107 mediated inhibition. Recently a strong inhibitor of cyclin D1/cdk4 kinase activity, $p27^{kip1}$, was isolated (Polyak et al., 1994; Toyoshima and Hunter, 1994). We also studied the effect of $p27^{kip1}$ expression on cyclin D1/cdk4 in the assay described above FIG. 18B shows that whereas cyclin D1/cdk4 effectively related p107 inhibition of E2F-4, co-transfection of a $p27^{kip1}$ expression vector completely blocked the release by cyclin D1/cdk4. Thus, inhibition of kinase activity of cyclin D1/cdk4 by either mutation of cdk4 or co-expression of $p27^{kip1}$ prevented the release of p107 inhibition. These data lend further support to the notion that cyclin D1/cdk4 kinase activity is required to release p107 inhibition of E2F-4.

Cyclin D1/cdk4 complexion phosphorylate p107

The effect of cyclin D1/cdk4 could be the result of phosphorylation of the E2F-4 protein, the p107 protein, or both. Although we have recently sown that E2F-4 is a phosphoprotein, we did not see any alterations in E2F-4 phosphorylation upon expression of cyclin D1/cdk4 neither in the absence not presence of p107 (Beijersbergen et al., 1994b and data not shown). We therefore focused on the effect of cyclin D1/cdk4 on p107. The cell cycle-regulated phosphorylation of pRb can be readily detected because of the increased apparent molecular weight of hyperphosphorylated pRb in SDS-acrylamide gels (Buchkovich et al., 1989; Ludlow et al., 1989). To study the effect of cyclin D1/cdk4 on p107 phosphorylation, we transfected the osteosarcoma cell line U2-OS with either an epitope-tagged p107 expression vector alone, or cotransfected with the dominant negative form of cdk4, cyclin D1/cdk4. Two days after transfection cells were lysed and whole cell extracts were subjected to 7.5% polyacrylamide SDS gel electrophoresis and the p107 protein was detected by Western blot analysis with 12CA5 antibody directed against HA-tagged p107. It was found that p107 migrates as a doublet when expressed in U2-OS cells. This doublet is reduced to a single band that migrates with the lower apparent molecular weight species when the dominant-negative form of cdk4 is co-expressed. This result suggests that the p107 protein is phosphorylated upon expression in U2-OS cells and that this phosphorylation can be abolished by the co-expression of a dominant-negative form of cdk4. Cotransfection of cyclin D1/cdk4 resulted in an increase of p107 species with higher apparent molecular weight (lane 4), most likely as a result of phosphorylation of p107 by cyclin D/cdk4. U2-OS cells express multiple p107 species probably as a result of endogenous kinase activity present in these cells. We searched for additional cell lines that lack significant p107 kinase activity. It was founded that C33A cervical carcinoma cells only express a single species of p107, which co-migrates with the faster migrating species of p107 in U2-OS cells. As expected, co-transfaction of cyclin D1/cdk4 resulted in a slower migrating species of p107. In contrast, contransfection of p107 with cyclin E/cdk2, or cyclin A/cdk2 did not result in a significant increase in p107 mobility. This lack of phosphorylation of p107 by cyclin E/cdk2 in C33A cells correlates with the absence of the release of the p107 mediated inhibition of E2F-4 transactivation in the same cells. U2-OS cells that were labeled with $[^{32}P]$-orthophosphate after transfection with HA tagged p107 alone or together with the different cyclin/cdk combinations, showed as increase in the amount of $[^{32}P]$-labeled p107 only in the presence of cyclin D1/cdk4 and not cyclin E/cdk2 or cyclin A/cdk2 (data not shown). To show that the increase in apparent molecular weight of p107 is the result of phosphorylation, we treated p107 immunoprecipitates with lambda phosphatase. p107, immunoprecipitated from U2-OS cells transfected with HA tagged p107, displays different p107 molecular weight species. Lambda phosphatase treatment of p107 immunoprecipitates resulted in the appearance of a single band that co-migrates with the faster migrating p107 species. A p107 immunoprecipitate treated with lambda phosphatase in the presence of phosphatase inhibitors contained both the slower and faster migrating species of p107 protein. We conclude that p107 is phosphorylated in vivo, most likely due to cyclin D-associated kinase activity and that expression of cyclin D1/cdk4 leads to hyperphosphorylation of p107.

Phosphorylation of p107 prevents interaction with E2F-4

To address whether p107 hyperphosphorylation results in a loss in association with the E2F-4/DP-1 heterodimeric complex, we performed the following experiment. An epitope tagged DP-1 expression vector was co-transfected with E2F-4 and p107 expression vectors in the presence or absence of cyclin/cdk expression vectors. Two days after transfection, cells were metabolically labeled with $[^{34}S]$-methionine and lysed in non ionic detergent. One half of each lysate was immunoprecipitated with p107 antibodies the other half with the 12CA5 antibody directed against HA tagged DP-1. Immunoprecipitated proteins were resolved on a low percentage acrylamide SDS gel, it was found that in the absence of co-transfected cyclin/cdks, the DP-1/E2F-4 heterodimer is bound to p107. Expression of cyclin D1/cdk4, completely abolished this interaction whereas expression of cyclin E/cdk2 did not cause a release of p107 from E2F-4. Thus, cyclin D1/cdk4-mediated phosphorylation of p107 prevents an interaction between p107 and the E2F-4/DF-1 heterodimer, whereas the expression of cyclin E/cdk2 does not affect the complex.

U2-OS cells contain both hypo-and hyperphosphorylated species of p107 protein. The experiments described above, indicate that phosphorylation of p107 prevents association with E2F-4, therefore p107 species that are associated with E2F-4 should be in the hypophosphorylated state. To address the phosphorylation status of p107 protein that is bound to E2F-4, we transfected U2-OS cells with HA-tagged E2F-4 alone or together with DF-1. Cells were lysed and E2F-4 protein was immunoprecipitated with 12CAS5 antibody directed against HA-E2F-4. As a control for the p107 species present in cells transfectant with both HAE2F-4 and DP-1, p107 proteins was immunoprecipitated with p107 antibody SD4. The immunoprecipitated proteins were separated on a low percentage polyacrylamide SDS gel and p107 protein was detected by Western blot with a p107 antibody. It was found that both species of p107 were again present in these cells. In contrast, p107 that was co-immunoprecipitated with HAE2F-4 only consisted of the faster migrating species. These results indicate that E2F-4 preferentially associates with the hypophosphorylated p107 species. Together we can conclude that p107 is phosphorylated, most likely by cyclin D/cdk4 kinase complexes, and that phosphorylation of p107 prevents the association between E2F-4 and p107.

p107 phosphorylation is cell cycle-regulated.

To study whether p107 is phosphorylated in a cell cycle-dependent fashion, we studied the phosphorylation status of p107 in untransfected NIH 3T3 fibroblasts. NIH 3T3 cells were made quiescent by culturing for 40 hours in low serum (0.2%). After this period the cells were re-stimulated with 10% serum and serum-stimulated cells were harvested at different time points. Cell extracts were subjected to low percentage polyacrylamide SDS-gel electrophoresis and p107 protein was detected by Western blot analysis, it was found that, quiescent cells express only the fastest-migrating species of p107. After 8 hours of serum stimulation, part of the p107 protein has shifted to a higher apparent molecular weight. After 10 hours, most p107 protein is of the slower-migrating species. In addition, we observed an increase in the amount of p107 after 10 hrs of serum stimulation. At this stage, we do not know whether this is the result of increased protein synthesis or protein stabilization as a result of phosphorylation. To examine the role of the D-type cyclins in the phosphorylation of p107, we analyzed that same extracts for cyclin D1 expression. As can be seen in FIG. 19, middle panel, cyclin D1 expression is induced at 6–8 hours after serum stimulation and remains constant at later time points. As a control we also analyzed the same extracts for the expression of cyclin E. It was found that cyclin E is not induced 12 to 14 hours after serum stimulation. These results indicate that phosphorylation of p107 a regulated in a cell cycle-dependent manner and that this phosphorylation takes place in the cell cycle shortly after cyclin D1 induction and well before cyclin E induction, suggesting the cyclin D is the most likely cyclin candidate to control p107 phosphorylation. To investigate how these difference in p107 phosphorylation affect E2F-p107 complex formation during the cell cycle, we analyzed E2F DNA binding complexes in the same 3T3 cells after serum stimulation. The most predominant complexes in G0 cells is E2F in complex with p130 (Cobrinik et al. 1993). In our experiments, the complexes did not change until 8 hours after serum stimulation and contain predominantly p130 as confirmed by p130 antibody dependent at supershifts (data not shown, Cobrinik et al. 1993). A more slowly migrating complex was first detected at 10 to 12 hours after serum stimulation. Only after time points of more than 18 to 24 hours, as cells being to pass from G1 into S-phase of the cell cycle (as determined by the flow cytometry, data not shown) the slowest migrating complex became prominent. To determine whether p107 was present in the slowly migrating complex, the same extracts were analyzed in the presence of a p107 antibody SDA. Between 10 and 16 hours after serum stimulation, very small amount of the supershifted complexes were detectable and remained constant. A 24 hours after serum stimulation, the majority of the higher order E2F complexes were supershifted by p107 antibody. When the presence of E2F complexes containing p107 was compared to the present of p107 protein in these cells it was seen that although there is a strong increase in the expression of phosphorylated p107 protein at time points 10–14 hours after stimulation this does not result in the increase in E2F/p107 complexes. The increase in E2F complexes containing p107 at later timepoints could indicate that at these timepoints, newly synthesized p107 protein is not longer phosphorylated and can therefore associated with E2F and form the E2F/p107 complex that is detected in S-phase cells.

Although p107 is phosphorylated when cells progress from G1 into S-phase of the cell cycle. E2F activity can be found associated with p107 in S-phase cells and asynchronously growing cells. We therefore asked whether hypophosphorylated p107, capable of forming a complex with E2F, is present in asynchronously growing cells. Both quiescent- and asynchronously growing 3T3 cells were analyzed for the presence of the different p107 species, it was found that, the level of p107 is much lower in G0 cells and only consists of the hypophosphorylated form. In asynchronously growing cells, much higher levels of p107 were detected and these cells contain both hypo-and hyperphosphorylated forms of p107. These results indicate that although p107 is phosphorylated in the G1 phase of the cell cycle after serum stimulation, a detectable amount of p107 remains under phosphorylated in the later stages of the cell cycle. This hypophosphorylated p107 is able to associate with E2F's, and is likely responsible for the p107-associated E2F activity detected in S-phase and in asynchronous cells.

Cyclin D1/cdk4 can rescue a p107-induced cell cycle block.

E2F transcription factors play an important role in the regulation of the G1- to S-phase transition. When transiently transfected, but pRb and p107 have the ability to arrest SAOS-2 cells in the G1-phase of the cell cycle (Zhu et al., 1993). The pRb-induced cell cycle block can be rescued by over-expression of cyclin A, cyclin E, cyclin D2 or D3, resulting in hyperphosphorylation of pRb (Hinds et al., 1992, Ewen et al., 1993). In contrast, a p107-induced cell cycle block cannot be rescued effectively by either cyclin A or cyclin E expression (Zhu et al. 1993). The data described above are in agreement with this, in that they show that p107 cannot be inactivated by ectopic expression of cyclin E. Since p107 inhibition of E2F-4 can be released by cyclin D1/cdk4, we asked whether expression of cyclin D1/cdk4 was able to release SAOS-2 cells from a p107-induced cell cycle block. SAOS-2 cells were transfected with the cell surface marker CD20 alone, with CD20 and p107 or with CD20, p107 and cyclin/cdk expression vectors. Three days after transfection, cells were selected for CD20 expression by FACS analysis and the cell-cycle distribution of transfected (CD20$^+$) cells was determined by propidium iodide staining.

Table 2 shows that expression of p107 in SAOS-2 cells resulted in a significant accumulation of CD20-positive cells in G1. Expression of cyclin D1/cdk4 completely released the p107-induced cell cycle block, decreasing the G1 population and increasing both 5 and G2/M phase cells. Consistent with the results of Zhu et al. (1993), we observed only a partial release of the P107 cell cycle block by cyclin E/cdk2 (Table 2). Additional controls with cyclin D3 alone or in combination with cdk2 or cdk4 showed that, as expected, only the cyclin D3/cdk4 complex was able to release the p107 cell cycle block. Taken together, our data indicate that p107 growth inhibitory activity in the cell cycle is regulated by D-type cyclins in association with cdk4, but not effectively by cyclin E and its associated kinase.

TABLE 2

Rescue of p107 induced cell cycle arrest in SA-OS2 cells by G1 cyclins.

| Rescue | vector | | | p107 | | |
|---|---|---|---|---|---|---|
|  | G1 | S | G2/M | G1 | S | G2/M |
|  | 47 | 12 | 41 | 73 | 6 | 21 |
|  | 42 | 15 | 43 | 67 | 9 | 24 |
|  | 44 | 14 | 42 | 61 | 10 | 29 |
| Cyclins |  |  |  |  |  |  |
| +pCMVcyclinD1/cdk4 | 35 | 22 | 42 | 38 | 24 | 38 |
|  |  |  |  | 37 | 16 | 23 |
| +pCMVcyclin E/cdk2 | 39 | 22 | 39 | 58 | 19 | 23 |
|  |  |  |  | 54 | 15 | 31 |
| +pCMVcyclinD3 |  |  |  | 54 | 14 | 31 |
| +pCMVcyclinD3/cdk4 |  |  |  | 34 | 18 | 48 |
| +pCMVcyclinD3/cdk2 |  |  |  | 56 | 13 | 31 |

Table 2 Rescue p107 induced cell cycle arrest in SAOS-2 cells by G1 cyclins. SAOS-2 cells were transfected with pCMV CD20 (2 µg) expression vector in combination with expression vectors pCMV or pCMVp107 (5 mg) together with different cyclins and cdks (10 µg each) as indicated. Transfected cells were analyzed by FACS and the cell cycle profile of CD20 positive cells was determined. The percentage of cells in G0/G1-phase, S-phase and G2/M-phase of the cell cycle are depicted.

Discussion

In this paper we present several lines of evidence to indicate that p107 is negatively regulated as a result of phosphorylation. The p107 protein is found to be differentially phosphorylated and this phosphorylation dramatically changes during the G1 to S-phase of the cell cycle to 3T3 fibroblasts.

p107 is a "pocket" protein that can form a complex with the cellular transcription factor E2F-4 in vivo. E2F-4 plays a role in the regulation of cell cycle progression (Beijersbergen et al., 1994, Ginsberg et al., 1994). The activity of the transcription factor E2F-4 can be suppressed by the expression of p107. Overexpression of p107 results in a G1 cell cycle arrest in certain cell types (Zhu et al., 1993). We show here that both the ability of p107 to interact with E2F-4 and the ability to induce a G1 cell cycle arrest are both abolished upon phosphorylation of p107. Furthermore, out experiments indicate that p107 is a target for cyclin D/cdk4 complexes.

In a first set of experiments, we studied the effects of cyclin/cdk complexes on the interaction between p107 and its E2F partner, E2F-4 (Beijersbergen et al., 1994b, Ginsberg et al., 1994). Transactivation by E2F-4 can be suppressed by expression of p107. Importantly, p107 suppression of E2F-4 could be released by co-expression of both cyclin D1 and cdk4, but not by either protein alone. This activity of cyclin D1/cdk4 was completely abolished when a dominant negative form of cdk4 was used or by co-expression of $p27^{kib1}$, a strong inhibitor of the cyclin D1/cdk4 kinase complex. Both these results indicate that cyclin D1-associated kinase activity is required to release p107 inhibition of E2F-4. Expression of cyclin D1/cdk4 caused hyperphosphorylation of p107 and resulted in a loss of association with E2F-4. In agreement with a role for cyclin D1 in phosphorylating p107 is the finding that p107 can be phosphorylated in vitro by cyclin D1/cdk4, Li et al., (1993) showed that p107 is found in complex with D type cyclins in vivo and in vitro kinase reactions with these complexes show that p107 can be phosphorylated by D type cyclin associated kinase activity. The binding of p107 and cyclin D, in analogy to cyclin D and pRb, suggest an alternative mechanism of D type cyclin action in that D type cyclins might interfere with both p107 and pRb function through direct binding to the pocket (Dowdy et al., 1993, Ewen et al., 1993, Hinds et al., 1993), thereby functionally inactivating p107 or pRb in the absence of phosphorylation. As discussed above, our data support a model in which p107 is inactivated through phosphorylation by the cyclin D/cdk4 complex and do not support the hypothesis that cyclin D1 acts by competing with E2F for p107 pocket binding.

Further evidence that phosphorylation of p107 is mediated by cyclin D complexes was obtained when we serum-stimulated quiescent fibroblasts: Phosphorylation of p107 occurs shortly after cyclin D1 is induced but well before cyclin E induction. Also, over-expression of a dominant negative form of cdk4 resulted in the disappearance of the hyperphosphorylated forms of p107 in U2-OS cells, strongly suggesting that D type cyclin associated kinase activity is responsible for this modification. Together, these data provide strong evidence that p107 is an in vivo substrate for cyclin D/cdk4. In agreement with the hypothesis that p107 is a target for cyclin D associated kinase activity is the finding that p107 phosphorylation as observed in U2-OS cells is absent in both SAOS-2 and C33A cells. The absence of p107 phosphorylation in C33A and SAOS-2 cells (which have only very little cyclin D-associated kinase activity), showing a correlation between the presence of cyclin D associated kinase activity and the phosphorylation status of p107 (RLB and RB, unpublished data).

Recent data show that cyclin D1 and cooperate with a mutant form of adenovirus E1A and an activated ras oncogene in the transformation of primary fibroblasts. Importantly, the GH mutant of cyclin D1 that had retained the ability to transform in this assay, was also able to release p107 inhibition of E2F. Conversely, the KE mutant of cyclin D1, which is unable to form a stable complex with cdk4, did not transform and did not release p107 inhibition of E2F-4. Thus, the ability of cyclin D1 mutants to transform segregates with the ability to inactivate p107. This suggests that cyclin D1 derives its oncogenic activity, at least in part, by releasing p107-associated proteins from their inactive, p107-board state. We and others have recently shown that p107 interacts with at least two cellular protein. E2F-4 and c MYC, both of which are endowed with oncogenic activity (Beijersbergen et al., 1994a, b; Ginsberg et al., 1994; Gu et al., 1994).

To our surprise, the cyclin E/cdk2 complex was unable to affect the complex between E2F-4 and p107. This result was unexpected because p107 forms a stable complex with cyclin E in vivo. In contrast to pRb, p107 contains within its pocket region a spacer that allows the formation of higher order complexes with cyclins and cdk's. These complexes contain apart from p107 and E2F (that interacts with the pocket region) cyclin A or cyclin E, together with their associated kinase cdk2. In spite of this, cyclin E/cdk2 mediated phosphorylation of p107 does not appear to occur in the E2F containing complex in vivo, at least not with the result that p107 is released from E2F. The role of the cyclin E/cdk2 complex in the p107/E2F complex therefore remains to be elucidated. It is a possibility that cyclin E/cdk2 is present in the p107/E2F complex to phosphorylate the E2F and/or the DP-1 component. Alternatively, cyclin E could be bound and inactivated by p107. In this scenario, p107 would act as a "molecular sink" to bind and inactivate cyclin E. Active cyclin E/cdk2 could then only occur above a certain threshold level of cyclin E. A similar threshold-setting role has recently been proposed for cdk inhibitory molecules (Peters, 1994) and we have recently obtained evidence to support a role for p107 in down-modulating cyclin A and E activity (Zhu et al 1995).

In S phase, p107 is found in complex with E2F and cyclin A (Lees et al., 1992). Cyclin A can also interact directly with E2F-1 resulting in the phosphorylation of at least one member of the E2F/DP complex (Krek et al., 1994, Dynlacht et al., 1994). This phosphorylation results in the down modulation of E2F-1 activity presumably through loss of DNA binding of the E2F-1/DP-1 complex, We did not find a release of p107 inhibition by cyclin A/cdk2 overexpression (data not shown). This indicates that like cyclin E/cdk2, cyclin A/cdk2 is also unable to inactivate p107 by phosphorylation.

Although hypophosphorylated p107 is present in G0, E2F complexes containing p107 are not readily detected. Instead E2F is found in complex with p130. Only after disappearance of the E2F-p130 complex, E2F/p107 complexes can be detected albeit at very low amounts. This could indicate that p130 can effectively compete with hypophosphorylated p107, which is present at this stage of the cell cycle, for binding to E2F-4. That p130 can bind E2F-4 was recently shown by us and others (RLB and RB, submitted for publication, Vairo et al, in press). The observation that p107 is phosphorylated at 8 hours after serum stimulation would suggest that at this moment newly synthesized E2F-4 would not be inactivated through the association with p107. At the same moment E2F/p130 complexes disappear. This would suggest a scenario in which E2F's that can be inactivated by p130 and p107 would now be free to activate transcription. On the other hand an increase in p107 containing E2F complexes is observed at the G1/S transition and throughout S-phase of the cell cycle, in our experiments at 18 hours post serum stimulation. The result of this regulation is that the p130 and p107 associated E2Fs are only free to activate transcription during a very small time frame from 8 to 18 hours following serum stimulation, before and after which the higher order complexes are present. The formation of these higher order complexes may play an important role in the active repression of genes when cells progress to the later stages of the cell cycle. A possible explanation for the re-occurrence of E2F/p107 complexes at S-phase, is that there is a strong increase in p107 protein expression. The majority of this newly synthesized protein is phosphorylated, but as a result of a decrease in cyclin D-associated kinase activity, a significant amount of p107 remains hypophosphorylated in S-phase. This newly synthesized hypophosphorylated p107 can form a complex with E2F-4.

Overexpression of p107 in SAOS-2 cells results in a growth arrest in the G1 phase of the cell cycle (Zhu et al., 1993). This p107-induced growth arrest could be rescued by cotransfection of cyclin D1/cdk4 or cyclin D3/cdk4 (Table 2). Thus, phosphorylation of p107 by cyclin D1/cdk4 does not only lead to the release of E2F-4, but inactivates virtually completely the growth suppressive activity of p107. In contrast, cyclin E/cdk2 only resulted in a partial release of the p107 cell cycle block. Thus, the different ability of cyclins D and E to release E2F-4 from p107 is correlated with their ability to inactivate the growth inhibitory activity of p107. Cellular targets of p107 may therefore play an important role in the progression of G1 to S phase. Consistent with this, both E2F-4 and c-MYC can stimulate S phase entry (Eilers et al., 1991; Beijersbergen et al., 1994b).

Our data reveal significant differences in substrate specificity between the two most prominent G1 cyclin-cdk complexes: p107 can be inactivated by D type cyclins and not by cyclin E, whereas pRb that can be inactivated by cyclin D2, D3 and E. Since cyclin D1 is induced prior to cyclin E in the cell cycle, our data also suggests that the p107-associated E2Fs are activated at an early point in G1, when cyclin D-associated kinase activity is induced. That p107E2Fs can function early in G1 is also supported by the recent findings that, in contrast to E2F-1, E2F-4 mRNA is already present in quiescent cells (Ginsberg et al., 1994; Johnson et al., 1994). Furthermore, E2 F-4 is transcriptionally induced prior to E2F-1 when cells progress through G1 into S (RLB and RB, unpublished data).

Even though cyclin E/cdk2 and cyclin D1/cdk4 complexes share many functional properties (Resnitzky et al., 1994; Ewen et al., 1993), a striking difference is that cyclin D1 is frequently involved in the genesis of human cancer, whereas little evidence for deregulated cyclin E expression in cancer exists to date. Our present data show that cyclin D1, when in complex with cdk4, can functionally inactivate p107, whereas cyclin E/cdk2 was inactive towards p107. It is possible that the higher oncogenic activity of cyclin D1 stems from its ability to inactivate the growth inhibitory activity of both pRb and p107, whereas over-expression of cyclin E would leave the p107-mediated growth inhibitory circuit intact.

MATERIALS AND METHODS FOR EXAMPLE 2

Cell lines

Human C33A, U2-OS and SAOS-2 were cultured in Dulbecco's modified Eagle's medium (DMEM) with 10% fetal calf serum. NIH 3T3 cells were cultured in Dulbecco's modified Eagle's medium (DMEM) with 10% newborn calf serum. Transfections were performed using the calcium phosphate precipitation technique (Graham and Van der Eb, 1973).

Synchronization of cells

NIH 3T3 cells were allowed to grow 24 hrs, and were then incubated with DMEM containing 0.2% serum for 40 hours. Re-stimulation of quiescent cells was performed by incubation with DMEM containing 10% serum for the indicated times.

Plasmids pCMVp27 was generated by the polymerase chain reaction using p27-specific primers of DNA isolated from a BALB/c bran cDNA library. DNA Sequencing showed that the amplified p27 cDNA was identical to the published sequence (Toyoshima and Hunter, 1994). PCMVHA E2F-4 was generated by cloning the haemagglotinin epitope tag at the $NH_2$-terminus of E2F-4 in pCMV. The plasmids pCMVpRb, pCMVp107, pCMVp107DE, pCMVCD20, pCMFE2F-4, pCMV-E2F-1, pCMV-DP-1, pCMV cyclin E, cyclin A, cyclin D1, cyclin D2, cdk2, cdk4, cdk4 dominant negative, cyclin D1-GH and cyclin D1-KE have all been described elsewhere (Hinds et al., 1992, 1994; Zhu et al., 1993; Van den Heuvel and Harlow, 1993; Beijersbergen et al., 1994b).

Immunological reagents

For the experiments described here we used the monoclonal antibody RK13 directed against E2F-4. Antibodies against p107 (SD2, SD4, SD9, SD6 and SD15) and against the HA epitope (12CA5) have been described previously (Field et al., 1988; Zhu et al., 1993). The antibody used for the detection of endogenous p107 in western, C-18, and cyclin E, C-19, were obtained from Santa Cruz. Cyclin D1 was detected by DSC-6 antibody from Sanbio.

CAT assays

C33A cells were transiently transfected with the expression vectors as indicated together with 2 μg E2F$_4$CAT (Helin et al., 1993), 0.2 μg RSVluciferase. pRc/CMV was added to a total of 20 μg DNA per 10-cm plate. Cells were harvested forty hours after transfection. Cells were collected and resuspended in 100 μl 0.1 M Tris-HCl, pH 8.0. Cells were freeze/thawed three times and centrifuged at 15,000 g at 4° C. for 10 min. Supernatants were assayed for luciferase activity (Promega, Luciferase system) and CAT activity using the phase extraction assay (Seed and Sheen, 1988). In all experiments, CAT activity was normalized to luciferase activity.

Phosphatase treatment

Immunoprecipitates were washed twice in phosphatase buffer (50 mM Tris-HCl, pH 7.8 and 5 mM DTT) and resuspended in 60 μl phosphatase buffer. Lambda phosphatase (NEB, 400 units) were added, where indicated, and incubated for 60 min at 30° C. Phosphatase inhibitors NaF (5 mM) and Na$_3$VO4 (5 mM) were added where indicated.

Metabolic labeling and immunoprecipitations

Cells were incubated for 1 hour in methionine-free DMEM in the presence of 10% fetal calf serum, followed by an incubation in methionine-free DMEM supplemented with 250 μCi Trans [$^{35}$S]-label for 4 hours. After labeling, cells were lysed in ELB$^+$buffer (ELB buffer containing 5 mM EDTA, 1 mM DTT, 10 mM NaF, 10 mM sodium orthovanadate, 0.2 mM sodium pyrophosphate, 1 μg/ml chymostatin and aprotinin and 1 mM phenylmethylsulfonylfluoride) and immunoprecipitated as described previously (Beijersbergen et al., 1994a).

Western blot analysis Cells were lysed in SDS-containing sample buffer and sonicated for 10 seconds. The cell extracts were then separated on SDS polyacrylamide gels and transferred to nitrocellulose. The membrane was blocked in TBST (1 5mM NaCl, 10 mM Tris-HCl pH 8.0 and 0.05% Tween-20 ) containing 5% dried milk for 16hours at 4° C. The membrane was then washed and the antibody was detected using horseradish peroxidase-linked goat anti rabbit IgG and enhanced chemiluminescence (Amersham). HA tagged p107 was detected with the 12CA56 monoclonal antibody at 1:1000 dilution, cyclin D1 with DSC-6 in 1:250 dilution and cyclin E with C-19 in 1:500 dilution in TBST containing 1% dried milk.

Mobility shift assays

For the preparation of whole cell extracts of quiescent or serum stimulated 3T3 cells, 10 cm tissue culture dishes were washed with cold PBS, cells were collected and resuspended in 100 μl of lysis buffer (20 mM Hepes, pH7.9, 0.4 MNaCl, 1 mM EDTA, 10 mM DTT, 1 mM phenylmethylsulfonyl fluoride (PMSF) and 25% glycerol. The cells were kept on ice for 20 min and lysed by two freeze thaw cycles (–80° C. and 0° C.). After centrifugation for 10 min at 15,000 rpm at 4° C., the supernatant was stored at 80° C. Gel shifts were performed using 10 μg of cells extract in a 20 μl reaction volume containing 10 mM Hepes, pH7.9, 100 mM KCl, 1 mM EDTA, 1 mM DTT, 4% Ficoll and 1 μg sonicated and boiled salmon sperm DNA. Where indicated SD9 antibody (Santa cruz) was added to the reaction mixture. Reactions were incubated for 10 min at room temperature (RT) after which 0.5 ng of $^{32}$P-labeled oligonucleotide containing the consensus E2 F DNA binding site (Santa cruz) was added and the reaction was incubated for an additional 20 min at RT. The reaction products were separated on a 3.5% polyacrylamide gel in 0.25 x TBE at 100V for 3 hrs at room temperature. The gel was then dried, and subjected to autoradiography.

SAOS-2 cell cycle block rescue

SAOS-2 cells were transfected using calcium phosphate precipitates containing 30 μg of plasmid DNA for each 15 cm dish. After 16 hours the cells were washed twice with DMEM/10% FCS and incubated with fresh medium at 37° C. Forty-eight hours later the cells were collected in PBS containing 3 mM EDTA, spun down and incubated with 20 μl of FITC conjugated anti CD20 monoclonal antibody (Becton-Dickinson) for 20 min. on ice. The cells were washed and fixed in 80% ethanol at 4° C. Before FACS analysis the cells were washed with PBS supplemented with 0.1% serum, and incubated with 20 μg/ml propidium iodide and 200 μg/ml RNAse A. The FACS analysis was performed on a Becton-Dickinson FACScan apparatus. A gate was set to select CD20-positive cells with a fluorescence intensity of more than 20-fold the control population. The propidium iodide signal was used to determine the cell cycle distribution of the selected cells.

References

Ajchembaum, F., Ando, K., DeCaprio, J. A. and Griffin, J. D. (1993). Independent regulation of human D-type cyclin gene expression during G1 phase in primary human T lymphocytes. J. Biol. Chem. 268, 4113–4119.

Ayer, D. E., L. Kretzner, and R. N. Eisenman 1993. Mad: A heterodimeric partner for Max that antagonizes Myc transcriptional activity. Cell 72: 211–222.

Baldin, V., Lukas, J., Marcote, M. J., Pagano, M. and Draetta, G. (1993). Cyclin D1 is a nuclear protein required for cell cycle progression in G1 . Genes, Dev. 7, 812–821.

Bandara, L. R., Buck, V. M., Zamanian, M., Johnston, L. H. and La Thangue, N. B. (1993). Functional synergy between DP-1 and E2 F-1 in the cell cycle regulating transcription factor DTRF1/E2 F1. EMBO J. 12, 4317–4324.

Bates, S., Parry, D., Bonetta, L., Vousden, K., Dickson, C. and Peters, G. (1994). Absence of cyclin D/cdk complexes in cells lacking functional retinoblastoma protein. Oncogene 9; 1633–1640.

Beijersbergen, R. L., Kerkhoven, R., Zhu, L., Carlée, L., Voorhoeve, P. M. and Bernards, R. (1994b). E2F-4, a new member of the E2F gene family, has oncogenic activity and associates with p107 in vivo. Genes, Dev. 8, 2680–2690.

Beijersbergen, R. L., E. M. Hijmans, I. Zhu, and R. Bernards 1994. Internaction of c-Myc with the pRb-related protein p107 results in inhibition of c-Myc-mediated transactivation. EMBO J. 17: 4080–4086.

Blanar, M. A. and W. J. Rutter 1992. Interaction cloning: Identification of a helix-loop-helix zipper protein that interacts with c-fos. Science 256: 1014–1018.

Buchkovich, K., L. A. Duffy, and E. Harlow 1989. The retinoblastoma protein is phosphorylated during specific phases of the cell cycle. Cell 58: 1097–1105.

Cao, L., Faha, B., Dembski, M., Tsai, L-H., Harlow, E and Dyson N. 1992. Independent binding of the retinoblastoma protein and p107 to the transcription factor E2F. Nature 355: 176–179.

Chellappan, S. P.; S. Hiebert, M. Mudryj, J. M. Horowitz, and J. R. Nevins 1991. The E2F transcription factor is a cellular target for the pRb protein. Cell65: 1053–1061.

Chen, P. L., P. Scully, J. Y. Shew, J. Y. Wang, and W. H. Lee 1989. Phosphorylation of the retinoblastoma gene product is modulated during the cell cycle and cellular differentiation. Cell 58: 1193–1198.

Cobrinik, D., P. Whyte, D. S. Peeper, T. Jacks, and R. W. Weinberg 1993. Cell cycle-specific associated of E2F with the p130 E1A-binding protein. Genes & Dev. 7: 2392–2404.

DeCaprio, J. A., J. W. Ludlow, D. Lynch, Y. Furukawa, J. Griffin, H. Piwnica-Worms, C. M. Huang, and D. M. Livingston 1989. The product of the retinoblastoma gene has properties of a cell cycle regulatory element. Cell 58: 1085–1095.

Dowdy, F. D., Hinds, P. W., Louie, K., Reed, S. I. and Weinberg, R. A. (1993). Physical interaction of the retinoblastoma protein with Human D cyclins. Cell. 73, 499–511.

Dulic, V., Lees, E. and Reed, S. I. (1992). Association of human cyclin E with a periodic G1-S phase protein kinase. Science 257, 1958–1961.

Dynlacht, B. D., Flores, O., Lees, J. A. and Harlow, E. (1994). Differential regulation of E2F transactivation by cyclin/cdk2 complexes. Genes Dev. 8, 1772–1786.

Dyson, N., M. Dembski, A. Fattaey, C. Ngwu, M. Ewen, and K. Helin, 1993. Analysis of p107-associated proteins: p107 associates with a form of E2F that differs from pRb-associated E2F-1. J. Virol. 67: 7641–7647.

Ellers, M., Schirm, and J. M. Bishop, 1992. The Myc protein activates transcription of the α-prothymosin gene. EMBO J. 10: 133–141.

Ewen, M. E., Faha, B., Harlow, E. and Livingston, D. M. (1992). Interaction of p107 with cyclin A independent of complex formation with viral oncoproteins. Science. 255, 85–87.

Ewen, M. E. Sluss, H. K., Sherr, C. J., Matsushime, H., Kato, J. and Livingston, D. M. (1993). Functional interactions of the retinoblastoma protein with mammalian D-type cyclins. Cell. 73, 487–497.

Farnham, P. J., J. E. Slansky, and R. Kollmar. 1993. The role of E2F in the mammalian cell cycle. Biochem. Biophys. Acta 1155: 125–131.

Field, J., Nikawa, J. K., Broek, D., MacDonald, B., Rodgers, L., Wilson, I. A., Lerner, R. A. and Wigler, M. (1988). Purification of a ras-responsive adenylyl cyclase complex from Saccharomyces cerevisiae by use of an epitope addition method. Mol. Cell. Biol. 8, 2159–2165.

Ginsberg, D., Vairo, G., Chittenden, T., Xiao, Z.-X., Xu, G., Wydner, K. L., DeCaprio, J. A., Lawrence, J. B. and Livingston, D. M. (1994). E2F-4, a new member of the E2F transcription factor family, interacts with p107. Genes, Dev. 8, 2665–2679.

Girling, R., J. F. Partridge, L. R. Bandara, N. Burden, N. F. Totty, J. J. Hsuan, and T. N. La, 1993. A new component of the transcription factor DRTF1/E2F. Nature 362: 83–87.

Graham, F. L. and Van der Eb, A. J. (1973). A new technique for the assay of infectivity of human adenovirus 5 DNA. Virology. 52, 456–467.

Gu W., Bhatia, L. T. Magrath, C. V. Dang, and R. Dalla-Favera. 1994. Binding and suppression of the Myc transcriptional activation domain by p107. Science 264; 251–254.

Hamel, P. A., R. M. Gill, R. A. Philips, and B. R. Gallie, 1992. Transcriptional repression of the E2-containing promoters ELLA, c-myc, and RM1 by the product of the RB1 gene, Mol. Cell. Biol. 12: 3431–3438.

Hannon, G. J., D. Demetrick, and D. Beach, 1993. Isolation of the Rb-related p130 through its interaction with CDK2 and cyclins. Genes & Dev. 7: 2378–2391.

Heikkila, R., G. Schwab, E. Wickstrom, S. Loke, D. Pluznik, R. Watt, and L. Neckers. 1987. A c-myc antisense oligodeoxy-nucleotide inhibits entry into S phase but not progress from G0 to G1. Nature 328: 445–449.

Helin, K., J. A. Lees, M. Vidal, N. Dyson, E. Harlow, and A. Fattaey 1992. A cDNA encoding a pRB-binding protein with properties of the transcription factor E2F. Cell 70:337–350.

Helin, K., E. Harlow, and A. Fattaey 1993a. Inhibition of E2F.1 transactivation by direct binding of the retinoblastoma protein. Mol. Cell. Biol. 13: 6501–6508.

Helin, K., C. L. Wu, A. R. Fattaey, J. A. Lees, B. D. Dynischt, C. Ngwu, And E. Harlow. 1993b Heteroimerization of the transcription factor E2F-1 and DP-1 leads to cooperative trans-activation factor. Genes & Dev 7: 1850–1861.

Hiebert, S. W., S. P. Chellappan, J. M. Horowitz, and J. R. Nevins. 1992. The interaction of RB with E2F concides with an inhibition of the transcriptional activity of E2P, Genes & Dev. 6: 177–185.

Hijmans, E. M., Voorhoever, P. M., Beijersbergen, R. L. and Bernards, R. (1995) E2F-5, a new E2F family member that interacts with p130 in vivo, Mol. Cell. Biol. In press.

Hinds, P. W., Mittnacht, S., Dulic, V., Arnold, A., Reed, S. I. and Weinberg, R. A. (1992). Regulation of retinoblastoma protein functions by ectopic expression of human cyclins. Cell. 70, 993–1006.

Hinds, P. W., Dowdy, S. F., Eaton, E. N., Arnold, A. and Weinberg, R. A. (1994). Function of a human cyclin gene as an oncogene. Proc Natl Acad Sci USA. 91, 709–713.

Hu, Q., C. Bautista, G. Edwards, D. Defeo-Jones, R. Jones, and E. Harlow, 1991). Antibodies specific for the human retinoblastoma protein identify a family of related polypeptides. Mol. Cell. Biol. 11: 5792–5799.

Huber, H. E. G. Edward, P. J. Goodhart, D. R. Patrick, P. S. Huang, H. M. Ivey, S. F. Barnett, A. Oliff and D. C. Heimbrook. 1993. Transcription factor E2F binds DNA as a heterodimer. Proc. Natl. Acad. Sci. 90: 3525–3529.

Ivey-Hoyle, M., R. Conroy, H. E. Huber, P. J. Goodhart, A. Oliff, and D. C. Heimbrook. 1993. Cloning and characterizaytion of E2F-2: A novel protein with biochemical properties of transcription factor E3F. Mol. Cell. Biol. 13: 7802–7812.

Jiang, W., Kahn, S. M., Tomita, N., Zhang, Y. J., Lu, S. H. and Weinstein, I. B. (1992). Amplification and expression of the human cyclin D gene in esophageal cancer. Cancer Res. 52, 2980–2983.

Johnson, D. G., Ohtani, K. and Nevins, J. R. (1994). Autoregulatory control of E2F1 expression in response to positive and negative regulators of cell cycle progression. Genes, Dev. 8, 1514–1525.

Johnson, D. G., J. K. Schwarz, W. D. Cress and J. R. Nevins, 1993. Expression of transcription factor E2F1 induces quiescent cells to enter S phase, Nature 365: 349–352.

Kaelin, W. G., W. Krek, W. R. Sellers, J. a. DeCaprio, F. Ajcherbaum, C. S. Fuchs, T. Chittenden, Y. Li. F. Earnharn, M. A. Blanar, D. M. Livingston, and E. K. Flemington. 1992. Expression cloning of a cDNA encoding a retinoblastoma-binding protein with E2F-like properties. Cell 70: 351–364.

Kamb, A., Gruis, N. A., Weaver-Feldhaus, J., Liu, Q., Harshman, K., S. V, T., Stolkert, E, Day, R. S., Johnson, B. E. and Skolnick, M. H. (1994). a cell cycle regulator potentially involved in genesis of many tumor types. Science. 264, 436–440.

Kato, J., Matsushime, H., Hiebert, S. W., Ewen, M. E. and Sherr, C. J. (1993). Direct binding of cyclin D to the retinoblastoma gene product (pRb) and pRb phosphorylation by the cyclin D-dependent kinase CDK4. Genes, Dev. 7, 331–342.

Koff, A., Giordano, A., Desai, D., Yamashita, K., Harper, J. W., Elledge, S., Nishimoto, T., Morgan, D. O., Franza, B. R. and Roberts, J. M. (1992). Formation and activation of a cyclin E-cdk2 complex during the G1 phase of the human cell cycle. Science. 257, 1689–1694.

Krek, W., D. M. Livingston and S. Shirodkar. 1993. Binding to DNA and the retinoblastoma gene product promoted by complex formation of different E2F family members. Science 262: 1557–1560.

Krek, W., M. E. Ewen, S. Shirodkar, Z. Arany, W. G. Kaelin, Jr., and D. M. Livingston. 1994. Negative regulation of the growth promoting transcription factor E2F-1 by a stably bound cyclin A dependent protein kinase. Cell 78: 161–172.

Lam, E. W. and R. J. Watson. 1993 An E2F-1 binding site mediates cell-cycle regulated repression of mouse β-myb transcription. EMBO J. 12: 2705–2713.

Lammie, G. A., Fantl, V., Smith, R., Schuuring, E., Brookes, S., Michalides, R., Dickson, C., Arnold, A. and Peters, G. (1991). D11S287, a putative oncogene on chromosome 11q13, is amplified and expressed in squamouse cell and mammary carcinoma and linked to BCL-1. Oncogene. 6, 439–444.

Land, H., L. F Parada, and R. A. Weinberg, 1983. Tumorigenic conversion of primary embry fibroblasts requires at least two cooperating oncogenes. Nature 304:596–602.

Lees, E. B. Paha, V. Dulie, S. J. Reed, and E. Harlow, 1992, Cyclin E/cdk2 cyclin A/cdk2 kinases associate with p107 and E2F in a temporally distinct manner. Genes & Dev. 6: 1874–1885.

Lees, J. A., M. Snito, M. Vidal, M. Valentine, T. Look, E. Harlow, N. Dyson and K. Helin. 1993. The retinoblastoma protein binds to a family of E2F transcription factors, Mol. Cell. Biol. 13: 7813–7825.

Li, L. J., G. S. Naeve, and A. S. Lee 1993a. Tempral regulation of cyclin A-p107 and p33cdk2 complexes binding to a human thymidine kinase promoter element important for G1-S phase transcriptional regulation. Proc. Natl. Acad. Sci. 90: 3554–3558.

Li. Y., C. Graham, S. Lacy, A. M. V. Duncan and P. Whyte. 1993b. The adenovirus E1a-associated 130-kD protein is encoded by a member of the retinoblastoma gene family and physically interacts with cyclins A and E. Genes & Dev. 7: 2366–2377.

Lovec, H., Sewing, A., Lucibello, F. C., Muller, R. and Moroy, T. (1994). Oncogenic activity of cyclin D1 revealed through cooperation with Ha-ras: link between cell cycle control and malignant transformation. Oncogene. 9, 323–326.

Ludlow, J. W., DeCaprio, J. A., Huang, C. M., Lee, W. H., Paucha, E. and Livingston, D. M. (1989). SV40 large T antigen binds preferentially to an underphosphorylated member of the retinoblastoma susceptibility gene product family. Cell. 56, 57–65.

Lukas, J.,Pagano, M., Staskova, Z., Draetta, G. and Bartek, J. (1994). Cyclin D1 protein oscillates and is essential for cell cycle progression in human tumour cell lines. Oncogene. 9, 707–718.

Matsushime, H., Roussel, M. F., Ashmun, R. A. and Sherr, C. J. (1991). Colony-stimulating factor 1 regulates novel cyclins during the G1 phase of the cell cycle. Cell 65, 701–713.

Matsushime, H., Quelle, D. E., Shurtleff, S. A., Shibuya, M., Sherr, C. J. and Kato, J. (1994). D-type cyclin -dependent kinase activity in mammalian cells. Mol. Cell. Biol. 14, 2066–2076.

Moran, E. and M. B. Mathews, 1987. Multiple functional domains in the adenovirus E1A gene. Cell 48: 177–178.

Motokura, T., Bloom, T., Kim, H. G., Juppner, H., Ruderman, J. V., Kronenberg, H. M. and Arnold, A. (1991). A novel cyclin encoded by a bell-linked candidate oncogene. Nature350, 512–515.

Nevins, J. R. 1992 E2F: A link between the Rb tumor suppressor protein and viral oncoproteins. Science 258:424–429.

Ohtsubo, M. and Roberts, J. M. (1993). Cyclin-dependent regulation of G1 in mammalian fibroblasts. Science 259, 1908–1912.

Peters, G. (1994). Stifled by inhibitors. Nature 371, 204–205.

Polyak, K., Lee, M. H., Erdjument, B. H., Koff, A., Roberts, J. M., Tempst, P. and Massague, J. (1994). Cloning of p27Kip1, a cyclin-dependent kinase inhibitor and a potential mediator of extracellular antimitogenic signals. Cell 78, 59–66.

Quelle, D. E., Ashmun, R. A., Shrtleff, S. A., Kato, J. -y., Bar-Sagi, D., Roussel, M. F. and Sherr, C. J. (1993). Overexpression of mouse D-type cyclins accelerated G1 phase in rodent fibroblasts. Genes, Dev. 7, 1559–1571.

Resnitzky, D., Gossen, M., Bujard, H. and Reed, S. I. (1994). Acceleration of the G1/S phase transition by expression of cyclins D1 and E with an inducible system. Mol Cell Biol. 14, 1669–1679.

Rosenberg, C. L., Wong, E., Petty, E. M., Bale, A. E., Tsujimoto, Y., Harris, N. L. and Arnold, A. (1991). PRAD1, a candidate BCL1 oncogene: mapping and expression in centrocytic lymphoma. Proc Natl Acad Sci USA. 88, 9638–9642.

Ruley, W. E. 1983 Adenovirus E1A enables viral and cellular transforming genes to transform primary cells in culture Nature. 304: 602–606.

Schuuring, E., Verhoeven, E., Mooi, W. J. and Michalides, R. J. (1992a). Identification and cloning of two overexpressed genes, U21B31/PRAD1 and EMS1, within the amplified chromosome 11q13 region in human carcinomas. Oncogene 7, 355–361.

Schuuring, E., Verhoeven, E., van, T. H., Peterse, J. L., Nunnink, B., Thunnissen, F. B., Devilee, P., Cornelisse, C. J., van de Vijver, M. J, Mooi, W. J. et. al. (1992b). Amplification of genes within the chromosome 11q13 region is indicative of poor prognosis in patients with operable breast cancer. Cancer Res. 52, 5229–5234.

Schwarz, J. K., S. H. Devoto, E. J. Smith, S. P. Chellappan, L. Jakoi and J. R. Nevins. 1993. Interactions of thep 107 and Rb proteins with E2F during the cell proliferation response. EMBO J. 12: 1013–1020.

Seed, B. and Sheen, J. Y. (1988). A simple phase-extaction assay for chloramphenicol acetyltransferase activity. Gene 67, 271–277.

Serrano, M., Hannon, G. and Beach, D. (1993). A new regulatory motif in cell cycle control causing specific inhibition of cyclin D/cdk4. Nature 366, 704–707.

Seto, M., Yamamoto, K., Iida, S., Akao, Y., Utsumi, K. R., Kubonishi, I., Miyoshi, I., Ohtsuki, T., Yawata, Y., Namba, M. et. al. (1992). Gene rearrangement and overexpression of PRAD1 in lymphoid malignancy with t(11;14)(q13; q32) translocation. Oncogene 7, 1401–1406.

Sewing, A., Burger, C., Brusselbach, S., Schalk, C., Lucibello, F. C. and Muller, R. (1993). Human cyclin D1 encodes a labile nuclear protein whose synthesis is directly induced by growth factors and suppressed by cyclic AMP. J Cell Sci. 104, 545–554.

Sherr, C. J. (1993). Mammalian G1 cyclins. Cell. 73, 1059–1065.

Shirodkar, S., M. Ewen, J. A. DeCaprio, J. Morgan, D. M. Livingstone and T. Chittenden, 1992, the transcription factor E2F interacts with the retinoblastoma product and a p107 cyclin A complex in a cell cycle regulated manner. Cell 68: 157–166.

Tam, S. W., Theodoras, A. M., Shay, J. W., Draetta, G. F. and Pagano, M. (1994). Differential expression and regulation of cyclin D1 protein in normal and tumor human cells: association with cdk4 is required for cyclin D1 function in G1 progression. *Oncogene* 9; 2663–2674.

Toyoshima, H. and Hunter, T. (1994). 27, a novel inhibitor of G1 cyclin-Cdk protein kinase activity, is related to p21. Cell. 78, 67–74.

Vairo, G., Livingston, D. M. and Ginsberg D. (1995). Functional interaction between E2F-4 and p130: evidence for distinct mechanisms underlying growth suppression by different retinoblastoma protein family members. *Genes & Dev*. In press.

van den Heuvel, S., and Harlow, E. (1993). Distinct roles for cyclin dependent kinases in cell cycle control. Science 262, 2050–2054.

Van der Eb A. J. and F. L. Graham, 1980. Assay of transforming activity of tumor virus DNA. Methods Enzymol. 65: 826–839.

Wang, T. C., Cardiff, R. D., Zukerberg, L., Lees, E., Arnold, A. and Schmidt, E. V. (1994). Mammary hyperplasia and carcinoma in MMTV-cyclin D1 transgenic mice. Nature. 369, 669–671.

Weintraub, S. J., C. A. Prater, And D. C. Dean 1992. Retinoblastoma protein switches the E2F site from positive to negative element. Nature. 358: 259–261.

Wimmel, A., Lucibello, F. C., Sewing, A., Adolph, S. and Muller, R. (1994). Inducible acceleration of G1 progression through tetracycline-regulated expression of human cyclin E. Oncogene 9, 995–997.

Withers, D. A., Harvey, R. C., Faust, J. B., Melnyk, O., Carey, K. and Meeker, T. C. (1991). Characterization of a candidate bcl-1 gene. Mol Cell Biol. 11, 4846–4853.

Won, K. A., Xiong, Y., Beach, D. and Gilman, M. Z. (1992). Growth-regulated expression of D-type cyclin genes in human diploid fibroblasts. Proc Natl Acad Sci USA, 89, 9910–9914.

Zamanian, M. and N. B. La Thangue, 1993. Transcriptional repression by the Rb related protein p107. Mol. Biol. Cell 4: 389–396.

Zhu, L., S. van den Heuvel, K. Helin, A. Fattaey, M. Ewen, D. Livingston, N. Dyson and E. Harlow, 1993. Inhibition of cell proliferation by p107, a relative of the retinoblastoma protein. Genes & Dev. 7: 1111–1125.

Zhu, L., Enders, G., Lees, J. A., Beijersbergen, R. L., Bernards, R. and Harlow, E. (1995). The pRb related protein p107 contains two growth suppression domains: Independent interactions with E2F and cyclin-cdk complexes. EMBOJ. In press.

---

What is claimed is:

1. A polynucleotide which comprises:
   (a) a sequence of nucleotides shown in SEQ ID NO; 1;
   (b) a sequence fully complementary to (a);
   (c) a sequence capable of selectively hybridising to a sequence in either (a) or (b), said sequence encoding a polypeptide which forms a trans-activation complex with DP-1 protein;
   (d) a sequence encoding a polypeptide which comprises the amino acid sequence of SEQ ID NO: 2; or
   (e) a fragment of any of the sequences in (a) to (d), said fragment encoding a polypeptide which forms a trans-activation complex with DP-1 protein.

2. A polynucleotide according to claim 1 which is a DNA polynucleotide.

3. A polynucleotide according to claim 1 wherein the sequence or fragments comprises at least 20 nucleotides.

4. A polynucleotide according to claim 1 which comprises the cDNA sequence of SEQ ID NO: 1.

5. A double stranded polynucleotide comprising a polynucleotide according to claim 1 and its complementary sequence.

6. A polynucleotide according to claim 1 carrying a revealing or detectable label.

7. A vector comprising a polynucleotide according to claim 1.

8. A host cell comprising a vector according to claim 7.

9. A host cell transformed by a vector according to claim 7 wherein the polynucleotide is operably linked to a control sequence capable of providing for the expression of the coding sequence by the host cell.

10. A vector which is a recombinant replicable vector comprising a coding sequence which encodes a polypeptide which comprises the amino acid sequence of SEQ ID NO: 2.

11. A host cell transformed by, or transfected with, a recombinant vector according to claim 10.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 1489 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 27..1268

(xi) SEQUENCE DESCRIPTION: SEQ ID NO: 1:

```
CAGTCGACCC CGGGGCGGCG GGCGCG ATG GCG GAG GCC GGG CCA CAG GCG CCG        53
                            Met Ala Glu Ala Gly Pro Gln Ala Pro
                              1               5

CCG CCC CCG GGG ACT CCA AGC CGG CAC GAA AAG AGC CTG GGA CTG CTC       101
Pro Pro Pro Gly Thr Pro Ser Arg His Glu Lys Ser Leu Gly Leu Leu
 10              15                  20                  25

ACC ACC AAG TTC GTG TCC CTT CTG CAG GAG GCC AAG GAC GGC GTG CTT       149
Thr Thr Lys Phe Val Ser Leu Leu Gln Glu Ala Lys Asp Gly Val Leu
                 30                  35                  40

GAC CTC AAG CTG GCA GCT GAC ACC CTA GCT GTA CGC CAG AAG CGG CGG       197
Asp Leu Lys Leu Ala Ala Asp Thr Leu Ala Val Arg Gln Lys Arg Arg
             45                  50                  55

ATT TAC GAC ATT ACC AAT GTT TTG GAA GGT ATC GGG CTA ATC GAG AAA       245
Ile Tyr Asp Ile Thr Asn Val Leu Glu Gly Ile Gly Leu Ile Glu Lys
         60                  65                  70
```

-continued

| | |
|---|---|
| AAG TCC AAG AAC AGC ATC CAG TGG AAG GGT GTG GGG CCT GGC TGC AAT<br>Lys Ser Lys Asn Ser Ile Gln Trp Lys Gly Val Gly Pro Gly Cys Asn<br>75                    80                    85 | 293 |
| ACC CGG GAG ATT GCT GAC AAA CTG ATT GAG CTC AAG GCA GAG ATC GAG<br>Thr Arg Glu Ile Ala Asp Lys Leu Ile Glu Leu Lys Ala Glu Ile Glu<br>90                    95                   100               105 | 341 |
| GAG CTG CAG CAG CGG GAG CAA GAA CTA GAC CAG CAC AAG GTG TGG GTG<br>Glu Leu Gln Gln Arg Glu Gln Glu Leu Asp Gln His Lys Val Trp Val<br>               110                   115               120 | 389 |
| CAG CAG AGC ATC CGG AAC GTC ACA GAG GAC GTG CAG AAC AGC TGT TTG<br>Gln Gln Ser Ile Arg Asn Val Thr Glu Asp Val Gln Asn Ser Cys Leu<br>         125                   130               135 | 437 |
| GCC TAC GTC ACT CAT GAG GAC ATC TGC AGA TGC TTT GCT GGA GAT ACC<br>Ala Tyr Val Thr His Glu Asp Ile Cys Arg Cys Phe Ala Gly Asp Thr<br>            140                  145              150 | 485 |
| CTC TTG GCC ATC CGG GCC CCA TCA GGC ACC AGC CTG GAG GTG CCC ATC<br>Leu Leu Ala Ile Arg Ala Pro Ser Gly Thr Ser Leu Glu Val Pro Ile<br>155                    160                   165 | 533 |
| CCA GAG GGT CTC AAT GGG CAG AAG AAG TAC CAG ATT CAC CTG AAG AGT<br>Pro Glu Gly Leu Asn Gly Gln Lys Lys Tyr Gln Ile His Leu Lys Ser<br>170                    175                   180               185 | 581 |
| GTG AGT GGT CCC ATT GAG GTT CTG CTG GTG AAC AAG GAG GCA TGG AGC<br>Val Ser Gly Pro Ile Glu Val Leu Leu Val Asn Lys Glu Ala Trp Ser<br>               190                   195               200 | 629 |
| TCA CCC CCT GTG GCT GTG CCT GTG CCA CCA CCT GAA GAT TTG CTC CAG<br>Ser Pro Pro Val Ala Val Pro Val Pro Pro Pro Glu Asp Leu Leu Gln<br>         205                   210               215 | 677 |
| AGC CCA TCT GCT GTT TCT ACA CCT CCA CCT CTG CCC AAG CCT GCC CTA<br>Ser Pro Ser Ala Val Ser Thr Pro Pro Pro Leu Pro Lys Pro Ala Leu<br>            220                   225               230 | 725 |
| GCC CAG TCC CAG GAA GCC TCA CGT CCA AAT AGT CCT CAG CTC ACT CCC<br>Ala Gln Ser Gln Glu Ala Ser Arg Pro Asn Ser Pro Gln Leu Thr Pro<br>         235                   240               245 | 773 |
| ACT GCT GTC CCT GGC AGT GCA GAA GTC CAG GGA ATG GCT GGC CCA GCA<br>Thr Ala Val Pro Gly Ser Ala Glu Val Gln Gly Met Ala Gly Pro Ala<br>250                    255                   260               265 | 821 |
| GCT GAG ATC ACA GTG AGT GGC GGC CCT GGG ACT GAT AGC AAG GAC AGT<br>Ala Glu Ile Thr Val Ser Gly Gly Pro Gly Thr Asp Ser Lys Asp Ser<br>               270                   275               280 | 869 |
| GGT GAG CTC AGT TCA CTC CCA CTG GGC CCA ACA ACA CTG GAC ACC CGG<br>Gly Glu Leu Ser Ser Leu Pro Leu Gly Pro Thr Thr Leu Asp Thr Arg<br>         285                   290               295 | 917 |
| CCA CTG CAG TCT TCT GCC CTG CTG GAC AGC AGC AGC AGC AGC AGC AGC<br>Pro Leu Gln Ser Ser Ala Leu Leu Asp Ser Ser Ser Ser Ser Ser Ser<br>         300                   305               310 | 965 |
| AGC AGC AGC AGC AGC AGC AAC AGT AAC AGC AGC AGT TCG TCC GGA CCC<br>Ser Ser Ser Ser Ser Ser Asn Ser Asn Ser Ser Ser Ser Ser Gly Pro<br>         315                   320               325 | 1013 |
| AAC CCT TCT ACC TCC TTT GAG CCC ATC AAG GCA GAC CCC ACA GGT GTT<br>Asn Pro Ser Thr Ser Phe Glu Pro Ile Lys Ala Asp Pro Thr Gly Val<br>330                    335                   340               345 | 1061 |
| TTG GAA CTC CCC AAA GAG CTG TCA GAA ATC TTT GAT CCC ACA CGA GAG<br>Leu Glu Leu Pro Lys Glu Leu Ser Glu Ile Phe Asp Pro Thr Arg Glu<br>               350                   355               360 | 1109 |
| TGC ATG AGC TCG GAG CTG CTG GAG GAG TTG ATG TCC TCA GAA GTG TTT<br>Cys Met Ser Ser Glu Leu Leu Glu Glu Leu Met Ser Ser Glu Val Phe<br>         365                   370               375 | 1157 |
| GCC CCT CTG CTT CGT CTT TCT CCA CCC CCG GGA GAC CAC GAT TAT ATC<br>Ala Pro Leu Leu Arg Leu Ser Pro Pro Pro Gly Asp His Asp Tyr Ile<br>         380                   385               390 | 1205 |

-continued

```
TAC AAC CTG GAC GAG AGT GAA GGT GTC TGT GAC CTC TTT GAT GTG CCT    1253
Tyr Asn Leu Asp Glu Ser Glu Gly Val Cys Asp Leu Phe Asp Val Pro
        395                 400                 405

GTT CTC AAC CTC TGACTGACAG GGACATGCCC TGTGTGGCTG GGACCCAGAC        1305
Val Leu Asn Leu
410

TGTCTGACCT GGGGGTTGCC TGGGGACCTC TCCCACCCGA CCCCTACAGA GCTTGAGAGC  1365

CACAGACGCC TGGCTTCTCC GGNATTNCCT TACCGCACAG TTCTGGCCAC ACGTCCCGCT  1425

CCTGTGCTGG CACTTCTGTG CTCGCAGAGC AGGGGAACAG GACTCAGCCC CCATCACCGT  1485

GGAG                                                              1489
```

(2) INFORMATION FOR SEQ ID NO: 2:

(i) SEQUENCE CHARACTERISTICS:
        (A) LENGTH: 413 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Glu Ala Gly Pro Gln Ala Pro Pro Pro Gly Thr Pro Ser
 1               5                  10                  15

Arg His Glu Lys Ser Leu Gly Leu Leu Thr Thr Lys Phe Val Ser Leu
                20                  25                  30

Leu Gln Glu Ala Lys Asp Gly Val Leu Asp Leu Lys Leu Ala Ala Asp
            35                  40                  45

Thr Leu Ala Val Arg Gln Lys Arg Arg Ile Tyr Asp Ile Thr Asn Val
        50                  55                  60

Leu Glu Gly Ile Gly Leu Ile Glu Lys Ser Lys Asn Ser Ile Gln
65                  70                  75                  80

Trp Lys Gly Val Gly Pro Gly Cys Asn Thr Arg Glu Ile Ala Asp Lys
                85                  90                  95

Leu Ile Glu Leu Lys Ala Glu Ile Glu Glu Leu Gln Gln Arg Glu Gln
            100                 105                 110

Glu Leu Asp Gln His Lys Val Trp Val Gln Gln Ser Ile Arg Asn Val
        115                 120                 125

Thr Glu Asp Val Gln Asn Ser Cys Leu Ala Tyr Val Thr His Glu Asp
    130                 135                 140

Ile Cys Arg Cys Phe Ala Gly Asp Thr Leu Leu Ala Ile Arg Ala Pro
145                 150                 155                 160

Ser Gly Thr Ser Leu Glu Val Pro Ile Pro Glu Gly Leu Asn Gly Gln
                165                 170                 175

Lys Lys Tyr Gln Ile His Leu Lys Ser Val Ser Gly Pro Ile Glu Val
            180                 185                 190

Leu Leu Val Asn Lys Glu Ala Trp Ser Ser Pro Val Ala Val Pro
        195                 200                 205

Val Pro Pro Glu Asp Leu Leu Gln Ser Pro Ser Ala Val Ser Thr
    210                 215                 220

Pro Pro Pro Leu Pro Lys Pro Ala Leu Ala Gln Ser Gln Glu Ala Ser
225                 230                 235                 240

Arg Pro Asn Ser Pro Gln Leu Thr Pro Thr Ala Val Pro Gly Ser Ala
                245                 250                 255

Glu Val Gln Gly Met Ala Gly Pro Ala Ala Glu Ile Thr Val Ser Gly
            260                 265                 270
```

```
Gly Pro Gly Thr Asp Ser Lys Asp Ser Gly Glu Leu Ser Ser Leu Pro
        275                 280                 285
Leu Gly Pro Thr Thr Leu Asp Thr Arg Pro Leu Gln Ser Ser Ala Leu
        290                 295                 300
Leu Asp Ser Ser Ser Ser Ser Ser Ser Ser Ser Ser Ser Ser Ser Asn
305                 310                 315                 320
Ser Asn Ser Ser Ser Ser Ser Gly Pro Asn Pro Ser Thr Ser Phe Glu
            325                 330                 335
Pro Ile Lys Ala Asp Pro Thr Gly Val Leu Glu Leu Pro Lys Glu Leu
            340                 345                 350
Ser Glu Ile Phe Asp Pro Thr Arg Glu Cys Met Ser Ser Glu Leu Leu
        355                 360                 365
Glu Glu Leu Met Ser Ser Glu Val Phe Ala Pro Leu Leu Arg Leu Ser
        370                 375                 380
Pro Pro Pro Gly Asp His Asp Tyr Ile Tyr Asn Leu Asp Glu Ser Glu
385                 390                 395                 400
Gly Val Cys Asp Leu Phe Asp Val Pro Val Leu Asn Leu
            405                 410
```